(12) United States Patent
Tapsak

(10) Patent No.: US 9,840,595 B2
(45) Date of Patent: Dec. 12, 2017

(54) SILICONE RUBBER

(71) Applicant: EMPIRE TECHNOLOGY DEVELOPMENT LLC, Wilmington, DE (US)

(72) Inventor: Mark Allan Tapsak, Orangeville, PA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/411,025

(22) PCT Filed: Jun. 17, 2013

(86) PCT No.: PCT/US2013/046120
§ 371 (c)(1),
(2) Date: Dec. 23, 2014

(87) PCT Pub. No.: WO2014/004146
PCT Pub. Date: Jan. 3, 2014

(65) Prior Publication Data
US 2015/0203635 A1 Jul. 23, 2015

Related U.S. Application Data

(60) Provisional application No. 61/663,787, filed on Jun. 25, 2012.

(51) Int. Cl.
| | | |
|---|---|---|
| *C08G 77/54* | (2006.01) | |
| *C08G 77/46* | (2006.01) | |
| *C08G 77/445* | (2006.01) | |
| *C08G 77/455* | (2006.01) | |
| *C08G 77/458* | (2006.01) | |
| *A61L 27/18* | (2006.01) | |
| *C07F 7/08* | (2006.01) | |

(52) U.S. Cl.
CPC ............. *C08G 77/54* (2013.01); *A61L 27/18* (2013.01); *C07F 7/0896* (2013.01); *C08G 77/445* (2013.01); *C08G 77/455* (2013.01); *C08G 77/458* (2013.01); *C08G 77/46* (2013.01)

(58) Field of Classification Search
CPC .............................. C08G 77/54; C08G 77/455
See application file for complete search history.

(56) References Cited

U.S. PATENT DOCUMENTS

| | | | | |
|---|---|---|---|---|
| 4,499,149 A | * | 2/1985 | Berger | .................. C07F 7/0889 257/788 |
| 4,605,712 A | * | 8/1986 | Mueller | .............. C08F 290/148 351/159.33 |
| 4,737,558 A | | 4/1988 | Falcetta et al. | |
| 4,826,752 A | | 5/1989 | Yoshida et al. | |
| 5,233,007 A | | 8/1993 | Yang | |
| 6,080,829 A | | 6/2000 | Tapsak et al. | |
| 6,534,587 B1 | | 3/2003 | Tapsak et al. | |
| 6,879,861 B2 | | 4/2005 | Benz et al. | |
| 7,071,279 B2 | | 7/2006 | Liao | |
| 7,632,876 B2 | | 12/2009 | Lai et al. | |
| 7,744,785 B2 | | 6/2010 | Phelan | |
| 8,283,429 B2 | | 10/2012 | Zhou et al. | |
| 2003/0216504 A1 | | 11/2003 | Wolfson et al. | |
| 2005/0090607 A1 | | 4/2005 | Tapsak et al. | |

FOREIGN PATENT DOCUMENTS

WO  WO2011112699 A1  9/2011

OTHER PUBLICATIONS

Gonzalez-Meijome et al., Refractive index and equilibrium water content of conventional and silicone hydrogel contact lenses, *Ophthal. Physiol. Opt.* (Jan. 2006), 26:57-64.
Kohnen et al., Experimental and clinical evaluation of incision size and shape following forceps and injector implantation of a three-piece high-refractive-index silicone intraocular lens, *Graefe's Archive for Clinical and Experimental Ophthalmology* (Sep. 1997), 236(12):922-928.
Radzinski et al., Synthesis of High Molecular Weight Poly (1, 1, 12, 12-tetramethyl-13-oxa-1, 12-disilatridecanylene-co-dimethylsiloxane) Using Anionic Ring-opening Polymerization, *Silicon* (Apr. 7, 2011), 3(2):57-62.
Tapsak et al., Preparation of Cyclosilalkylenesiloxane Monomers and their Cationic Ring Opening Polymerization, *Journal of Inorganic & Organometallic Polymers* (Mar. 1999), 9(1):35-53.
Tapsak et al., Synthesis and Microstructure Analysis of Poly(dimethylsiloxane-co-1,1,12,12-tetramethyl-13-oxa-1,12-disilatridecanylene), *Polymer Preprints* (2000), 41(1):572-573.
Tehrani et al., Material properties of various intraocular lenses in an experimental study, *Ophthalmologica* (2004), 218:57-63.
International Search Report and Written Opinion for PCT/US2013/046120 dated Nov. 1, 2013.
Andriot et al., Silicones in Industrial Applications, p. 106 (2007).
Blackburn et al., Studies on the refractive index of copoly(arylene-siloxane) constructed with amide, ester, or ether linkage units, Department of Chemistry, Bloomsburg University of Pennsylvania, Bloomsburg, p. 1 (Apr. 9, 2013).
Bruma et al., Silicon-Containing Aromatic Polymers, *Journal of Macromolecular Science-Polymer Reviews* (2001), C41(1-2):1-40.
Brunchi et al., High Performance Polymers, *Properties of Some Poly(siloxane)s for Optical Applications* (Mar. 4, 2008), SAGE, 21:31-47.
Chalk et al., Palladium-Catalyzed Vinyl Substitution Reactions. 11. Synthesis of Aryl Substituted Allylic Alcohols, Aldehydes,and Ketones from Aryl Halides and Unsaturated Alcohols, *J. Org. Chem.* (1976), 41(7):1206-1209.
Riegler et al., Optical Silicones for use in Harsh Operating Environments, *Silicon Technology* (Oct. 25-28, 2004), pp. 1-16.

* cited by examiner

Primary Examiner — Kuo-Liang Peng
(74) Attorney, Agent, or Firm — Pepper Hamilton LLP

(57) ABSTRACT

Copolymers, as well as compounds, compositions, articles of manufacture, and methods of making thereof, are disclosed. The copolymers may generally exhibit flexibility properties and may generally have a high refractive index. The copolymers may generally be made by providing a dihydrodisiloxane and an aliphatic vinyl alcohol and combining the dihydrodisiloxane and the aliphatic vinyl alcohol under conditions that allow for hydrogenation of the aliphatic vinyl alcohol and result in coupling of the aliphatic vinyl alcohol to the dihydrodisiloxane to produce a hydroxyl substituted siloxane.

21 Claims, 5 Drawing Sheets

SILICONE RUBBER

CROSS-REFERENCE TO RELATED APPLICATIONS

The present application is a National Stage filing under 35 U.S.C. §371 of International Patent Application PCT/US2013/046120, filed on Jun. 17, 2013 and entitled "SILICONE RUBBER", which claims priority to U.S. Provisional Application No. 61/663,787, filed on Jun. 25, 2012, and entitled "SILICONE RUBBER", the contents of which are incorporated herein in their entirety.

BACKGROUND

A typical problem with glass-based and polymer-based materials for use in a wide variety of products such as personal electronics displays, optics, display screens, lenses (for example, intraocular lenses), and the like is that they are highly susceptible to breakage due to impact velocity, torsional strain, compression, bending and the like.

Previous attempts to minimize this breakage have resulted in the advent of crystalline, polymer-based materials. However, the polymers that have been developed to date remain ill-suited for everyday use, as the crystalline structure is susceptible to cracking, fatigue and discoloration. Polymers that remedy this problem are somewhat opaque and do not have a sufficiently high refractive index to provide image clarity to users viewing objects through a display or lens. Accordingly, there still exists a need for novel polymer compositions that are highly flexible and/or have a high refractive index.

SUMMARY

Various embodiments are directed to compounds and compositions including a copolymer having the structure:

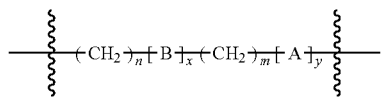

where A may be one or more silicon containing repeating units, B may be one or more aromatic ring containing or aliphatic cyclic ring containing repeating units, n and m may each be, independently, an integer of 1 to 10, and x and y may each be, independently, an integer from 1 to 2000. Compositions may further include one or more additional components, one or more additives, or combinations thereof.

Various embodiments are directed to a method for producing a copolymer, wherein the method may include providing a dihydrodisiloxane and an aliphatic vinyl alcohol and combining the dihydrodisiloxane and the aliphatic vinyl alcohol under conditions that allow for hydrogenation of the aliphatic vinyl alcohol and result in coupling of the aliphatic vinyl alcohol to the dihydrodisiloxane to produce a hydroxyl substituted siloxane.

Various embodiments may be directed to a method for preparing a copolymer, wherein the method may include providing aromatic diamine and an aliphatic vinyl carboxylic acid, combining the aromatic diamine and the aliphatic vinyl carboxylic acid under conditions that allow for coupling of the aromatic diamine and the aliphatic vinyl carboxylic acid to produce an aromatic diamine, combining the aromatic diamine with a chlorosilane under conditions that allow for coupling of the aromatic diamine and the chlorosilane to produce an aromatic bischlorosilane, and placing the aromatic bischlorosilane under conditions that allow for hydrolysis and condensation to create the copolymer.

Various embodiments may be directed to a method for preparing a copolymer, wherein the method may include the steps of providing an aromatic dihalide and an aliphatic vinyl alcohol, combining the aromatic dihalide and the aliphatic vinyl alcohol under conditions that allow for coupling of the aromatic dihalide and the aliphatic vinyl alcohol to produce an aromatic divinyl, combining the aromatic divinyl with a chlorosilane under conditions that allow for coupling of the aromatic divinyl and the chlorosilane to produce an aromatic bischlorosilane, and placing the aromatic bischlorosilane under conditions that allow for hydrolysis and condensation to create the copolymer.

Various embodiments may be directed to a method for producing a copolymer, wherein the method may include providing an aromatic dicarboxylic acid and an aliphatic vinyl alcohol, combining the aromatic dicarboxylic acid and the aliphatic vinyl alcohol under conditions that allow for coupling of the aromatic dicarboxylic acid and the aliphatic vinyl alcohol to produce an aromatic divinyl, combining the aromatic divinyl with a chlorosilane under conditions that allow for coupling of the aromatic divinyl and the chlorosilane to produce an aromatic bischlorosilane, and placing the aromatic bischlorosilane under conditions that allow for hydrolysis and condensation to create the copolymer.

Various embodiments are directed to articles of manufacture including a copolymer having the structure:

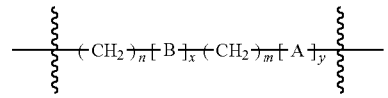

where A may be one or more silicon containing repeating units, B may be one or more aromatic ring containing or aliphatic cyclic ring containing repeating units, n and m may each be, independently, an integer of 1 to 10, and x and y may each be, independently, an integer from 1 to 2000.

Various embodiments are directed to ophthalmic lenses including a copolymer having the structure:

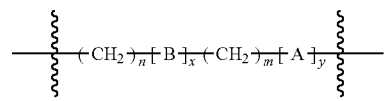

where A may be one or more silicon containing repeating units, B may be one or more aromatic ring containing or aliphatic cyclic ring containing repeating units, n and m may each be, independently, an integer of 1 to 10, and x and y may each be, independently, an integer from 1 to 2000.

Various embodiments are directed to a method of making a copolymer. The method may include contacting one or more silicon containing compounds with one or more reactive aromatic or aliphatic cyclic compound to form the copolymer.

DETAILED DESCRIPTION

Figure 1:
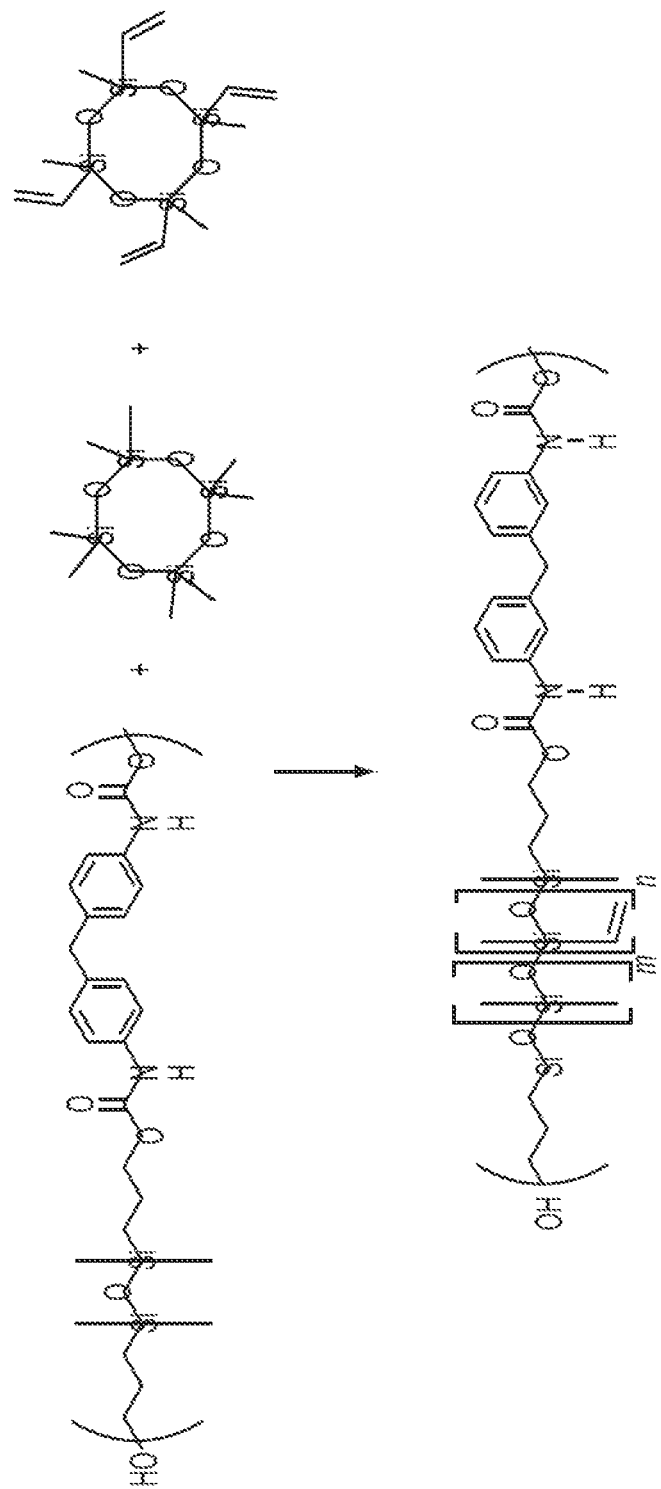
FIG. 1 depicts a chemical equation for combining a polymer having alternating siloxane units coupled to aromatic units with one or more cyclic siloxanes to produce a copolymer with additional siloxane fragments according to an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used in this document, the term "comprising" means "including, but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

A "refractive index" refers generally to a measurement of how radiation propagates through a medium. In general terms, a medium having a high refractive index (i.e., a refractive index greater than 1) for light waves passing through that medium may be visually clear to the human eye; thus, users viewing objects such as images and the like through a medium with a high refractive index will be able to clearly and easily see the objects as opposed to a medium with a lower refractive index.

A "display" or "electronic display" refers generally to a substrate used for the purposes of optics. Examples of displays may include screens and display components of electronic devices, optical lenses such as eyeglass lenses, telescope lenses, microscope lenses, contact lenses and the like, window panes or any other type of substrate that may be used for allowing visible light to pass therethrough. Examples of electronic devices that may incorporate an electronic display may include, but are not limited to, personal computers, gaming systems, televisions, and portable electronic devices such as smartphones, personal digital assistants, cameras, tablet computers, laptop computers, GPS navigation devices, media players and the like.

"Lens" or "Lenses" as used herein refers generally to any ophthalmic device that resides in or on the eye. The ophthalmic device can provide optical correction or may be cosmetic. For example, the term "lens" can refer to a contact lens, intraocular lens, overlay lens, ocular insert, optical insert or other similar device through which vision is corrected or modified, or through which eye physiology is cosmetically enhanced (e.g. iris color) without impeding vision.

Various embodiments are directed to aromatic silicone-based elastomer that are flexible and/or stretchable. Some embodiments are directed to compounds having a number of aromatic groups or aliphatic cyclic groups within the backbone of the elastomer that can elicit a higher refractive index and may be more transparent or have more optical clarity than current silicone-based compounds. Other embodiments are directed to aromatic silicon-based or aliphatic cyclic silicone-based compounds that have a very low glass transition temperature (e.g., less than 100 degrees Celsius) while at the same time having a high temperature stability (e.g., greater than 100 degrees Celsius). Other embodiments are directed to aromatic silicon-based or aliphatic cyclic silicone-based compounds that have a tensile strength of about 800-1500 psi. Thus, the elastomer disclosed herein may be particularly suited for applications requiring a high tensile strength, low glass transition temperature, high temperature stability, flexibility and optical clarity, including, but not limited to, displays, lenses and optics. In addition, due to the biocompatibility of silicone-based compounds in general, the elastomers disclosed herein which are also silicone-based, coupled with their high refractive indices and optical clarity, make them suitable as materials for lenses used in ophthalmic applications, for example, contact lenses and intraocular lenses.

While the disclosed embodiments focus primarily on the use of the compounds discussed herein in displays, lenses and optics, those skilled in the art may appreciate that other uses of the compounds are contemplated without departing from the scope of the disclosure.

Some embodiments may include copolymers including at least one silicon containing repeating unit and at least one aromatic ring containing or aliphatic cyclic ring containing repeating unit. For example, in some embodiments, the copolymers of the present disclosure may be of general Formula I:

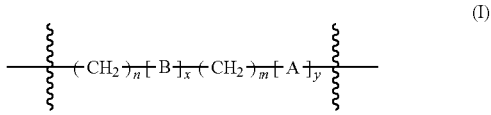

(I)

wherein A is a silicon containing repeating unit, B is an aromatic ring containing or aliphatic cyclic ring containing repeating unit, n and m are each, independently, an integer of 1 to 10, and x and y are each, independently, an integer from 1 to 2000.

The silicon containing repeating unit (A) may be any silicon containing repeating unit known in the art. For example, in various embodiments, the silicon containing repeating unit may be polydimethyl siloxane, alkoxysilane, chlorosilane, alkoxy silicate or combinations thereof. In particular embodiments, the silicon containing repeating unit may be units derived from tetraethylorthosilicate (TEOS), tetramethylorthosilicate (TMOS), 1,2-bis(trimethoxysilyl)ethane, octyltrimethoxysilane, tetraethyl silicate, tetraisopropyl silicate, tetramethyl silicate, tetramethoxysilane, tetraethoxysilane, tetraisopropoxysilane, propyltrimethoxysilane, ethyltrimethoxysilane, methyltrimethoxysilane, methyltriethoxysilane, aminoalkoxysilane, silicontetrachloride ($SiCl_4$), trichloro(dichloromethyl)silane ($Cl_2CHSiCl_3$), trichloro(hexyl)silane ($CH_3(CH_2)_5SiCl_3$), trichloro(isobutyl)silane (($CH_3)_2CHCH_2SiCl_3$), trichloro(octadecyl)silane ($CH_3(CH_2)_{17}SiCl_3$), trichlorooctylsilane, trichloro(phenethyl)silane ($C_6H_5CH_2CH_2SiCl_3$), trichloro(phenyl)silane, trichloro(propyl)silane, trichloro(methyl)silane, trichloro(chloromethyl)silane, dichloro(dimethyl)silane, isobutyl(trimethoxy)silane, 1,2-bis(dimethoxysilyl)ethane, octyldimethoxysilane, propyldimethoxysilane, ethyldimethoxysilane, methyldimethoxysilane, methyldiethoxysilane, dichloro(dichloromethyl)silane ($Cl_2CHSiHCl_2$), dichloro(hexyl)silane ($CH_3(CH_2)_5SiHCl_2$), dichloro(isobutyl)silane (($CH_3)_2CHCH_2SiCl_2$), dichloro(octadecyl)silane ($CH_3(CH_2)_{17}SiHCl_2$), dichlorooctylsilane, dichloro(phenethyl)silane ($C_6H_5CH_2CH_2SiHCl_2$), dichloro(phenyl)silane, dichloro(propyl)silane, dichloro(methyl)silane, dichloro(chloromethyl)silane, isobutyl(dimethoxy)silane, or combinations thereof.

The aromatic ring containing repeating unit (B) may be any aromatic containing repeating unit known in the art, and may further include one or more aromatic rings. For example, in some embodiments, the aromatic containing repeating unit may include repeating units derived from aromatic hydroxy carboxylic acid, aromatic dicarboxylic acid, aromatic diol, aromatic aminocarboxylic acid, aromatic hydroxyamine, aromatic diamine, aromatic diisocyanate, aromatic diester, aromatic diether, or combinations thereof. None of these classes of aromatic compounds are limited by this disclosure, and any aromatic containing compound may be used. In particular, examples of aromatic hydroxy carboxylic acids include, but are not limited to, 4-hydroxybenzoic acid, 3-hydroxybenzoic acid, 2-hydroxybenzoic acid, 2-hydroxy-6-naphthoic acid, 2-hydroxy-5-naphthoic acid, 2-hydroxy-7-naphthoic acid, 2-hydroxy-3-naphthoic acid, 4'-hydroxy phenyl-4-benzoic acid, 3'-hydroxy phenyl-4-benzoic acid, 4'-hydroxy phenyl-3-benzoic acid and alkyl, alkoxy or halogen substituents thereof or combinations thereof. In embodiments including substituted aromatic hydroxy carboxylic acids, alkyl and alkoxy substituents may have 1 to 6 carbon atoms, and halogen may include fluorine, chlorine, bromine, iodine, or combinations thereof. In particular embodiments, the aromatic hydroxy carboxylic acid may be 4-hydroxybenzoic acid and 2-hydroxy-6-naphthoic acid used alone or in combination. Examples of the aromatic dicarboxylic acids that can be incorporated into the copolymers of the invention include, but are not limited to, terephthalic acid, isophthalic acid, 2,6-naphthalenedicarboxylic acid, 1,6-naphthalenedicarboxylic acid, 2,7-naphthalenedicarboxylic acid, 4,4'-dicarboxybiphenyl, 3,4'-dicarboxybiphenyl, 4,4''-dicarboxyterphenyl, bis(4-carboxy phenyl)ether, bis(4-carboxy phenoxy)butane, bis(4-carboxy phenyl)ethane, bis(3-carboxy phenyl)ether and bis(3-carboxy phenyl)ethane and alkyl, alkoxy or halogen substituents thereof, or combinations thereof. In certain embodiments, the aromatic dicarboxylic acid may be terephthalic acid, isophthalic acid, 2,6-naphthalenedicarboxylic acid, or any combination thereof. Examples of aromatic diols that can be incorporated into the copolymers of the disclosed embodiments include, but are not limited to, hydroquinone, resorcinol, catechol, bisphenol, bisphenol F (bis(4-hydroxydiphenyl)methane), bisphenol A (2,2-bis(4-hydroxyphenyl)propane), 2,6-dihydroxynaphthalene, 2,7-dihydroxynaphthalene, 1,6-dihydroxynaphthalene, 3,3'-dihydroxybiphenyl, 3,4'-dihydroxybiphenyl, 4,4'-dihydroxybiphenyl, 4,4'-dihydroxy biphenol ether, bis(4-hydroxy phenyl)ethane, 2,2'-dihydroxy binaphthyl, and alkyl, alkoxy or halogen substituents thereof, or combinations thereof. In certain embodiments, the aromatic diol may be hydroquinone, resorcin, 4,4'-dihydroxybiphenyl, 2,6-dihydroxynaphthalene or any combination thereof. Examples of aromatic diethers that can be incorporated into the copolymers of the disclosed embodiments include, but are not limited to, diallyloxy benzene. Examples of aromatic diesters that can be incorporated into the copolymers of the disclosed embodiments include, but are not limited to, diallyl phthalate, diallyl isophthalate, or combinations thereof. Examples of aromatic diisocyanates that can be incorporated into the copolymers of the disclosed embodiments include, but are not limited to, methylene diisocyanate, toluene diisocyanate, or combinations thereof.

In some embodiments, the aliphatic cyclic ring containing repeating unit (B) may be any aliphatic cyclic ring containing repeating units known in the art, and may further include one or more aliphatic cyclic rings. For example, in some embodiments, the aliphatic cyclic ring containing repeating unit may include repeating units derived from cyclic hydroxy carboxylic acid, cyclic dicarboxylic acid, cyclic diol, cyclic aminocarboxylic acid, cyclic hydroxyamine, cyclic diamine, cyclic diisocyanate, cyclic diester, cyclic diether, or combinations thereof. In certain embodiments, the cyclic diisocyanate may be hydrogenated methylene diisocyanate.

In certain embodiments, the aromatic ring containing repeating unit may include repeating units derived from aromatic hydroxy carboxylic acid wherein the aromatic hydroxy carboxylic acid may be present in the copolymer at a concentration of about 5 weight percent to about 95 weight percent. In some embodiments, the aromatic ring containing repeating unit may include repeating units derived from aromatic hydroxy carboxylic acid wherein the aromatic hydroxy carboxylic acid may be present in the copolymer at a concentration of about 5 weight percent, about 10 weight percent, about 15 weight percent, about 20 weight percent, about 25 weight percent, about 30 weight percent, about 35 weight percent, about 40 weight percent, about 45 weight percent, about 50 weight percent, about 55 weight percent, about 60 weight percent, about 65 weight percent, about 70 weight percent, about 75 weight percent, about 80 weight percent, about 85 weight percent, about 90 weight percent, or about 95 weight percent. In particular embodiments, the aromatic ring containing repeating unit may include repeating units derived from aromatic hydroxy carboxylic acid wherein the aromatic hydroxy carboxylic acid may be present in the copolymer at a concentration of about 20 weight percent to about 80 weight percent.

In certain embodiments, the aromatic ring containing repeating unit may include repeating units derived from an aromatic dicarboxylic acid, wherein the aromatic dicarboxylic acid may be present in the copolymer at a concentration of about 0 or 0.05 weight percent to a concentration of about 45 weight percent. In some embodiments, the aromatic dicarboxylic acid may be present in the copolymer at a concentration of about 5 weight percent, about 10 weight percent, about 15 weight percent, about 20 weight percent, about 25 weight percent, about 30 weight percent, about 35 weight percent, about 40 weight percent, or about 45 weight percent. In particular embodiments, the aromatic ring containing repeating unit may include repeating units derived from an aromatic dicarboxylic acid, wherein the aromatic dicarboxylic acid may be present in the copolymer at a concentration of about 0 or 0.05 weight percent to about 25 weight percent.

In particular embodiments wherein the aromatic ring containing repeating unit includes repeating units derived from aromatic diols, the aromatic diol may include hydroquinone, 4,4'-dihydroxybiphenyl or 2,6-dihydroxynaphthalene. In some embodiments, hydroquinone, 4,4'-dihydroxybiphenyl or 2,6-dihydroxynaphthalene may provide increased reactivity during the polymerization process.

In certain embodiments, the aromatic ring containing repeating unit may include repeating units derived from aromatic hydroxyamines Examples of the aromatic hydroxyamines may include 4-amino phenol, N-methyl-4-amino phenol, 3-amino phenol, 3-methyl-4-amino phenol, 4-amino-l-naphthol, 4-amino-4'-hydroxy biphenyl, 4-amino-4'-hydroxy biphenyl ether, 4-amino-4'-hydroxy biphenyl methane, 4-amino-4'-hydroxy biphenyl sulfide and 2,2'-diamino binaphthyl. In particular embodiments, the aromatic hydroxyamine may be 4-amino phenol. In some embodiments, 4-amino phenol may contribute to a balance of properties of a resulting polymer.

In certain embodiments, the aromatic ring containing repeating unit may include repeating units derived from aromatic diols and/or aromatic hydroxyamines, wherein the aromatic diols and/or aromatic hydroxyamines may be present in the copolymer at a concentration of about 0 or 0.05 weight percent to about 45 weight percent. In some embodiments, the aromatic diols and/or aromatic hydroxyamines may be present in the copolymer at a concentration of about 5 weight percent, about 10 weight percent, about 15 weight percent, about 20 weight percent, about 25 weight percent, about 30 weight percent, about 35 weight percent, about 40 weight percent, or about 45 weight percent. In particular embodiments, the aromatic containing repeating unit may include repeating units derived from aromatic diols and/or aromatic hydroxyamines, wherein the aromatic diols and/or aromatic hydroxyamines may be present in the copolymer at a concentration of about 0 or 0.05 weight percent to about 25 weight percent.

In particular embodiments, the aromatic ring containing repeating unit may include at least one compound selected from the group consisting of aromatic dicarboxylic acids, aromatic diols and aromatic hydroxyamines. In some embodiments, aromatic dicarboxylic acids, aromatic diols and aromatic hydroxyamines may facilitate the generation of branched polymer chains upon the copolymerization due to a reaction with the trifunctional hydroxy naphthalene carboxylic acid represented by the general formula (I).

In some embodiments, the aromatic ring or aliphatic cyclic ring containing repeating unit may be copolymerized with other polymerizable monomers. Examples of such polymerizing or copolymerizing monomers may include aromatic diamines, aromatic aminocarboxylic acids, alicyclic dicarboxylic acids, aliphatic diols, alicyclic diols, aromatic mercapto carboxylic acids, aromatic dithiols, aromatic mercapto phenols and reactive derivatives thereof. In particular embodiments, the aromatic ring or aliphatic cyclic ring containing repeating unit may be copolymerized with aromatic diamines, aromatic aminocarboxylic acids, aliphatic diols or combinations thereof. In some embodiments, the copolymerizable monomers may be present in the copolymer at a concentration of about 0.05 weight percent to about 20 weight percent. In particular embodiments, the aromatic diamines, aromatic aminocarboxylic acids, aliphatic diols or combinations thereof may be present in the copolymer at a concentration of about 0 weight percent or about 0.05 weight percent to about 20 weight percent. In some embodiments, the aromatic diamines, aromatic aminocarboxylic acids, aliphatic diols or combinations thereof may be present in the copolymer at a concentration of about 5 weight percent, about 10 weight percent, about 15 weight percent or about 20 weight percent.

Examples of aromatic diamines and aromatic aminocarboxylic acids may include 1,4-phenylene diamine, 1,3-phenylene diamine, N-methyl-1,4-phenylene diamine, N,N'-dimethyl-1,4-phenylene diamine, 4,4'-diamino phenyl sulfide(thiodianiline), 4,4'-diamino biphenyl sulfone, 2,5-diamino toluene, 4,4'-ethylene dianiline, 4,4'-diamino biphenoxy ethane, 4,4'-diamino biphenyl methane(methylene dianiline), 4,4'-diamino biphenyl ether(oxydianiline), 4-amino benzoic acid, 3-amino benzoic acid, 6-amino-2-naphthoic acid and 7-amino-2-naphthoic acid. In particular embodiments, the aromatic diamine may be selected from a group consisting of 1,4-phenylene diamine and 1,3-phenylene diamine. In particular embodiments, the aromatic aminocarboxylic acid may be 4-amino benzoic acid.

Examples of alicyclic dicarboxylic acids, aliphatic diols and alicyclic diols may include hexahydro terephthalic acid and linear or branched aliphatic diols such as trans-1,4-cyclohexane diol, cis-1,4-cyclohexane diol, trans-1,4-cyclohexane dimethanol, cis-1,4-cyclohexane dimethanol, trans-1,3-cyclohexane diol, cis-1,2-cyclohexane diol, trans-1,3-cyclohexane dimethanol, ethylene glycol, propylene glycol, butylene glycol, 1,3-propane diol, 1,2-propane diol, 1,4-butane diol, 1,6-hexane diol and neopentyl glycol as well as reactive derivatives thereof. In particular embodiments, the aliphatic diols and alicyclic diols may be selected from a group consisting of ethylene glycol, propylene glycol and butylene.

Examples of aromatic mercapto carboxylic acids, aromatic dithiols and aromatic mercapto phenols may include 4-mercapto benzoic acid, 2-mercapto-6-naphthoic acid, 2-mercapto-7-naphthoic acid, benzene-1,4-dithiol, benzene-1,3-dithiol, 2,6-naphthalene-dithiol, 2,7-naphthalene-dithiol, 4-mercapto phenol, 3-mercapto phenol, 6-mercapto-2-hydroxynaphthalene, 7-mercapto-2-hydroxynaphthalene, reactive derivatives thereof, or combinations thereof.

In certain embodiments, the copolymer may be crosslinked, wherein one or more crosslinking agents or one or more curing agents may be used. Examples of the one or more crosslinking agents or the one or more curing agents may include, but are not limited to, an epoxy functional crosslinker, a phenolic functional crosslinker, a hydroxyl functional crosslinker, an amine functional crosslinker, a carboxylate functional crosslinker, an isocyanate functional crosslinker, or combinations thereof covalently associated with the copolymer.

In some embodiments, Formula I may be combined with one or more units of Formula II:

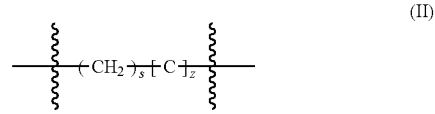

wherein C may be a unit derived from a crosslinker and also wherein C may be tetraethylorthosilicate (TEOS), tetramethylorthosilicate (TMOS), 1,2-bis(trimethoxysilyl)

ethane, octyltrimethoxysilane, tetraethyl silicate, tetraisopropyl silicate, tetramethyl silicate, tetramethoxysilane, tetraethoxysilane, tetraisopropoxysilane, silicontetrachloride ($SiCl_4$), trichloro(dichloromethyl)silane ($Cl_2CHSiCl_3$), trichloro(hexyl)silane ($CH_3(CH_2)_5SiCl_3$), trichloro(isobutyl)silane (($CH_3)_2CHCH_2SiCl_3$), trichloro(octadecyl)silane ($CH_3(CH_2)_{17}SiCl_3$), trichlorooctylsilane, trichloro(phenethyl)silane ($C_6H_5CH_2CH_2SiCl_3$), trichloro(phenyl)silane, trichloro(propyl)silane, trichloro(methyl)silane, trichloro(chloromethyl)silane, vinyltris(2-methoxyethoxy)silane, vinyltris isobutoxysilane, vinyltri-t-butoxysilane, vinyltriphenoxysilane, vinyltrimethoxysilane, vinyltriisopropoxysilane, vinyltriethoxysilane, vinyltriacetoxysilane, vinylmethyldiethoxysilane, vinylmethyldiacetoxysilane, vinyl bis(trimethylsiloxy)silane vinyldimethoxysilane, methylchlorosilane, methyldichlorosilane, methyltrichlorosilane, methylbromosilane, methyldibromosilane, methyltribromosilane, methylfluorosilane, methyldifluorosilane, methyltrifluorosilane, methyliodosilane, methyldiiodosilane, methyltriiodoosilane, methylchlorobromosilane, methylchlorofluorosilane, or combinations thereof. Furthermore, s may be an integer from 1 to 10 and z may be an integer from 1 to 10. In some embodiments, one or more units of Formula II may be randomly interposed within the copolymer. The resulting copolymer formed from the incorporation of Formula I and Formula II may have, for example, Formula (A):

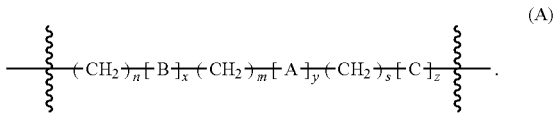

(A)

In some embodiments, Formula I may be combined with one or more units of Formula III:

(III)

wherein R may be an end group defining a terminus of the copolymer and also wherein R comprises vinyl, alkoxy, acetoxy, methoxy, amide, ester, carbamate, enoxy, oxime, amino, hydroxyl, cyano, halo, acrylate, epoxide, isocyanato, or combinations thereof. The resulting copolymer formed from the incorporation of Formula I and Formula III may have, for example, Formula (B):

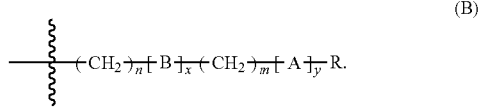

(B)

In some embodiments, the copolymers described herein may exhibit a generally high refractive index. Examples of a generally high refractive index may be a refractive index of about 1 to a refractive index of about 2.42. In some embodiments, the copolymers described herein may exhibit a refractive index of about 1.4 to about 1.5. In particular embodiments, the copolymers described herein may exhibit a refractive index of about 1, about 1.1, about 1.2, about 1.3, about 1.4, about 1.5, about 1.6, about 1.7, about 1.8, about 1.9, about 2, about 2.1, about 2.2, about 2.3 or about 2.4.

In some embodiments, the aromatic ring containing or aliphatic cyclic ring containing repeating unit (B) may include one or more linkage units that couple the aromatic ring or aliphatic cyclic ring to the silicon containing repeating unit (A). The linkage unit may be an amide linkage unit, an ester linkage unit, an ether linkage unit, or combinations thereof. In an embodiment, the linkage unit may be an amide linkage unit.

It will be appreciated that the coupling of the aromatic ring containing repeating unit or the aliphatic cyclic ring containing unit to the silicon containing repeating unit can result in copolymers that have higher refractive indices as compared to conventional PDMS or silicone-based materials. The type of linkage unit coupling the ring structure to the silicon containing repeating unit may further influence the refractive index of the material. For example, where the linkage unit is electron donating such as an amide linkage unit, the electron rich amide unit can donate electrons to the ring structure to increase the electron density within the ring structure. As a result of the increase in electron density, polarizability of the copolymer may increase and hence the refractive index exhibited by the copolymer may also increase. Where the linkage unit is an ester linkage unit, the electron withdrawing action of the ester linkage unit may result in a lower electron density within the ring structure as compared to when the linkage unit is an amide. Accordingly, the refractive index exhibited by such copolymers may be lower as compared to when the linkage unit is an amide, but will be higher than conventional PDMS or silicon-based materials due to the presence of the aromatic ring or aliphatic cyclic ring structure.

In some embodiments, the copolymers described herein may be incorporated within a composition, wherein the composition has one or more additional components, one or more additives, or combinations thereof. In particular embodiments, the one or more additional components or one or more additives may be selected from the group consisting of fillers, fumed silica fillers, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, impact agents, flame retardants, and the like, or combinations thereof.

In some embodiments, the copolymers described herein may be incorporated within an article of manufacture. Examples of articles of manufactures may include, but are not limited to, lenses, displays, optics, electronic devices, and the like.

In some embodiments, the copolymers described herein may be incorporated into compositions for making ophthalmic lenses such as contact lens, intraocular lens, overlay lens, ocular insert, optical insert or the like. The compositions may, for example, be molded to form ophthalmic lenses with selected curvatures and dimensions, depending on requirements of a user's eye. As the copolymers have high refractive indices and optical clarity, the ophthalmic lenses formed from such copolymers can provide image clarity to users viewing objects through the lenses.

The copolymers described herein may be synthesized by any process now known or later developed in the art. The elastomer may generally be synthesized by combining one or more silicon containing repeating units (A) with one or more aromatic ring containing or aliphatic cyclic ring containing repeating units (B).

In some embodiments, the copolymers described herein may be prepared by contacting one or more silicon containing compounds with one or more reactive aromatic or aliphatic cyclic compound to form the copolymer.

In some embodiments, the silicon containing compound may be as described above. For example, the silicon containing compound may be polydimethyl siloxane, alkoxysiloxane, chlorosilane, alkoxy silicate, or combinations thereof. Where the silicon containing compound is a polydimethyl siloxane, the polydimethyl siloxane may be hydroxyl terminated or hydride terminated.

In various embodiments, the reactive aromatic compound may include aromatic hydroxy carboxylic acid, aromatic dicarboxylic acid, aromatic diol, aromatic aminocarboxylic acid, aromatic hydroxyamine, aromatic diamine, aromatic diisocyanate, aromatic diester, aromatic diether, or combinations thereof. In some embodiments, the reactive aromatic compound may include an aromatic containing oligomer comprising two or more covalently linked monomeric aromatic groups.

In various embodiments, the reactive aliphatic cyclic compound may include cyclic dicarboxylic acids, cyclic diols, cyclic diisocyanates, cyclic hydroxy carboxylic acid, cyclic aminocarboxylic acid, cyclic hydroxyamine, cyclic diamine, cyclic diester, cyclic diether, or combinations thereof. In an embodiment, the cyclic diisocyanate may be a hydrogenated methylene diisocyanate.

In some embodiments, before contacting the silicon containing compound and the reactive aromatic or aliphatic cyclic compound, the silicon containing compound may be processed to remove water present therein. For example, the silicon containing compound may be contacted with a first solvent, and refluxed to remove the water. The first solvent can, for example, be toluene, xylene, benzene, or a combination thereof.

In some embodiments, contacting the silicon containing compound and the reactive aromatic or aliphatic cyclic compound may include adding a catalyst. The catalyst may be a metallic catalyst. For example, the metallic catalyst may include platinum, nickel, palladium, or combinations thereof. In some embodiments, the catalyst may be an organic catalyst. For example, the organic catalyst may be dibutylin dilaurate. Another example of the organic catalyst can be platinum-divinyltetramethyldisiloxane complex.

In some embodiments, combining the silicon containing compound and the reactive aromatic or aliphatic cyclic compound may include adding a second solvent. For example, the second solvent may be tetrahydrofuran, cyclohexane, or a combination thereof. The copolymer, when formed, may dissolve in the second solvent.

In some embodiments, the method of preparing the copolymer described herein may further include precipitating the copolymer from the second solvent. The precipitating step may include adding a third solvent to the copolymer and the second solvent. The third solvent may for example be methanol, ethanol or a combination thereof.

In some embodiments, the method of preparing the copolymer described herein may further include drying the precipitated copolymer. The drying can, for example, be performed in a vacuum oven or any other drying methods known in the art.

Further exemplary synthesis processes that are merely illustrative and not exhaustive are shown in the following schemes:

Scheme 1

In an embodiment a first synthesis step may include combining a dihydrodisiloxane with an aliphatic vinyl alcohol under conditions that allow for hydrogenation of the aliphatic vinyl alcohol and coupling of the aliphatic alcohol to the siloxane, as represented by the following equation:

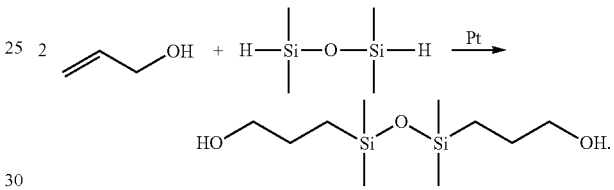

In scheme 1, the aliphatic vinyl alcohol is represented by allyl alcohol (prop-2-en-1-ol). Generally, such reactions can be carried out under pressure at a temperature of 200° C. in the presence of a metallic catalyst such as, but not limited to, platinum, nickel or palladium. The resulting hydroxyl substituted siloxane may then be combined with a reactive aromatic compound under conditions that allow coupling of the reactive aromatic compound to the hydroxyl substituted siloxane to produce a polymer having alternating siloxane units and aromatic containing units coupled through aliphatic carbamate units as represented by the following equation:

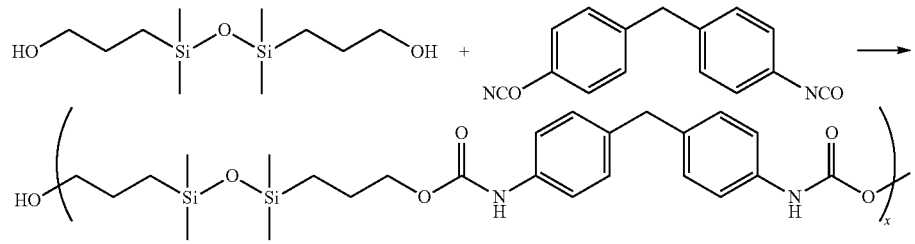

where x may be an integer from 1-200. The siloxane is the siloxane produced from the previous equation, the reactive aromatic compound is represented by bis(4-isocyanatophenyl)methane, and the two are linked through a carbamate linkage. In some embodiments, the reactive aromatic compound may include monomeric aromatic groups such as those described above, and in other embodiments, the reactive aromatic compound may be an aromatic containing oligomer including two or more monomeric aromatic groups with reactive termini. In still other embodiments, the coupling reaction described above may be carried out under conditions and with appropriate monomeric units and co-factors that allow for the in situ synthesis of an aromatic containing polymer from monomeric aromatic group precursors.

The polymer having alternating siloxane units coupled to aromatic units may then be combined with one or more cyclic siloxanes to produce a copolymer with additional siloxane fragments, as represented by the equation shown in FIG. 1. FIG. 1 depicts a polymer having siloxane repeating units coupled to aromatic containing repeating units is the carbamate linked polymer produced from the previous equation, and the cyclic siloxanes are represented by octamethylcyclotetrasiloxane and 1,3,5,7-tetravinyl-1,3,5,7-tetramethylcyclotetrasiloxane. In particular embodiments, the cyclic siloxanes may be in a solution comprising a ratio of about 1 part octamethylcyclotetrasiloxane to 4 parts 1,3,5,7-tetravinyl-1,3,5,7-tetramethylcyclotetrasiloxane by weight, wherein the octamethylcyclotetrasiloxane and 1,3,5,7-tetravinyl-1,3,5,7-tetramethylcyclotetrasiloxane, together, may be present in the solution at a concentration of about 80 percent by weight. In other embodiments, the copolymer may include m octamethylcyclotetrasiloxane repeating units and n 1,3,5,7-tetravinyl-1,3,5,7-tetramethylcyclotetrasiloxane repeating units, wherein m and n are each, independently, an integer greater than 4.

Scheme 2

Figure 2:
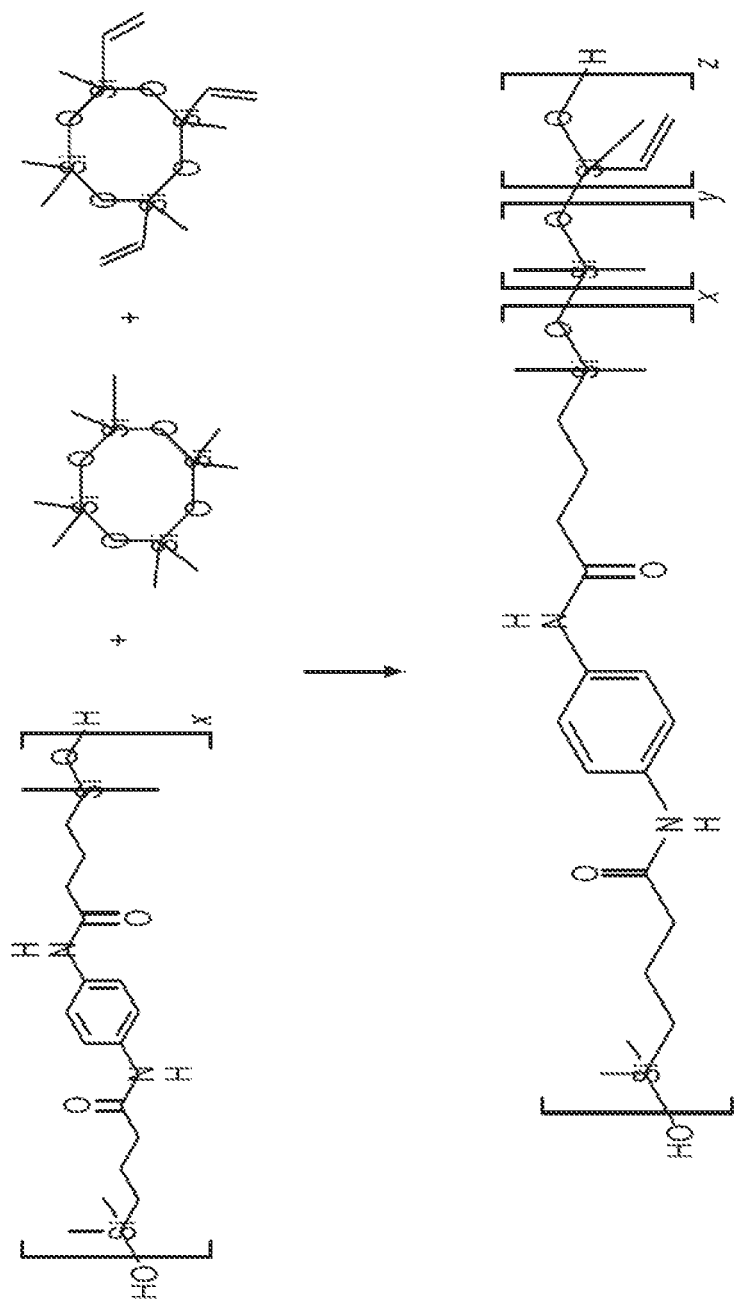
FIG. 2 depicts a chemical equation for combining a siloxane polymer with one or more cyclic siloxanes to produce a siloxane copolymer with additional siloxane groups according to an embodiment.

In an embodiment, a first synthesis step may include combining an aromatic diamine with an aliphatic vinyl carboxylic acid under conditions that may allow for a condensation reaction, as represented by the following equation:

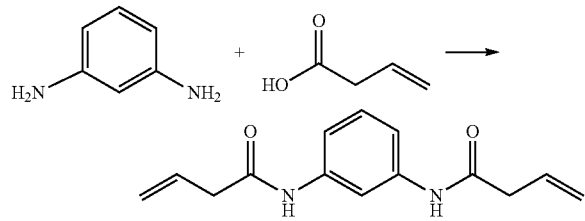

wherein the aromatic diamine is represented by benzene-1,4-diamine and the aliphatic vinyl carboxylic acid is represented by but-3-enoic acid to yield N,N'-(1,3-phenylene)dibut-3-enamide. Generally, such reactions may be carried out in a suitable solvent such as tetrahydrofuran under reflux for a minimum of two hours. The resulting diene may be combined with a chlorosilane, such as, in an embodiment, chlorodimethylsilane to obtain a bischlorosilane monomer, as represented by the following equation:

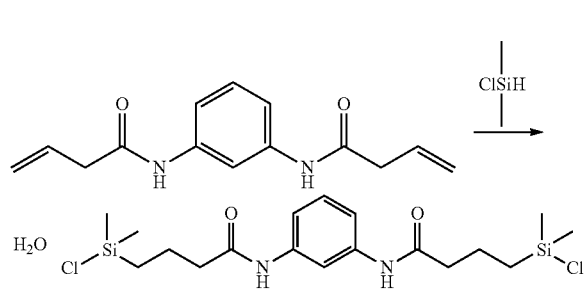

where the diene is N,N'-(1,3-phenylene)dibut-3-enamide and the bischlorosilane is N,N'-(1,3-phenylene)bis(4-(chlorodimethylsilyl)butanamide). In some embodiments, the bischlorosilane monomer, in the presence of water, may undergo hydrolysis followed by condensation reactions to obtain a siloxane polymer, as represented by the following equation:

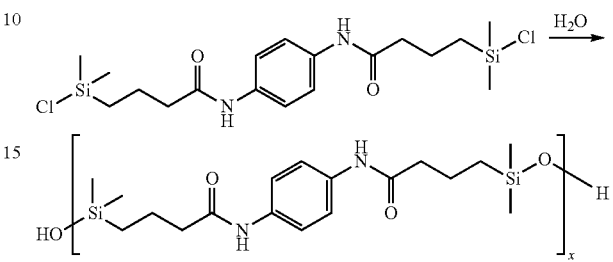

wherein x may be an integer from 1-200 and the siloxane polymer contains aromatic amides. The siloxane polymer may then be combined with one or more cyclic siloxanes to produce a siloxane copolymer with additional siloxane groups, as represented by the equation shown in FIG. 2. The siloxane polymer is the aromatic amide containing polymer produced from the previous equation, and the cyclic siloxanes are represented by octamethylcyclotetrasiloxane and 1,3,5,7-tetravinyl-1,3,5,7-tetramethylcyclotetrasiloxane. In particular embodiments, the cyclic siloxanes may be in a solution comprising a ratio of about 1 part octamethylcyclotetrasiloxane to 4 parts 1,3,5,7-tetravinyl-1,3,5,7-tetramethylcyclotetrasiloxane by weight, wherein the octamethylcyclotetrasiloxane and 1,3,5,7-tetravinyl-1,3,5,7-tetramethylcyclotetrasiloxane, together, may be present in the solution at a concentration of about 80 percent by weight. In other embodiments, the copolymer may include m octamethylcyclotetrasiloxane repeating units and n 1,3,5,7-tetravinyl-1,3,5,7-tetramethylcyclotetrasiloxane repeating units, wherein m and n are each, independently, an integer greater than 4. In some embodiments, x, y, and z may each, independently, be integers from 1-200.

Scheme 3

Figure 3:
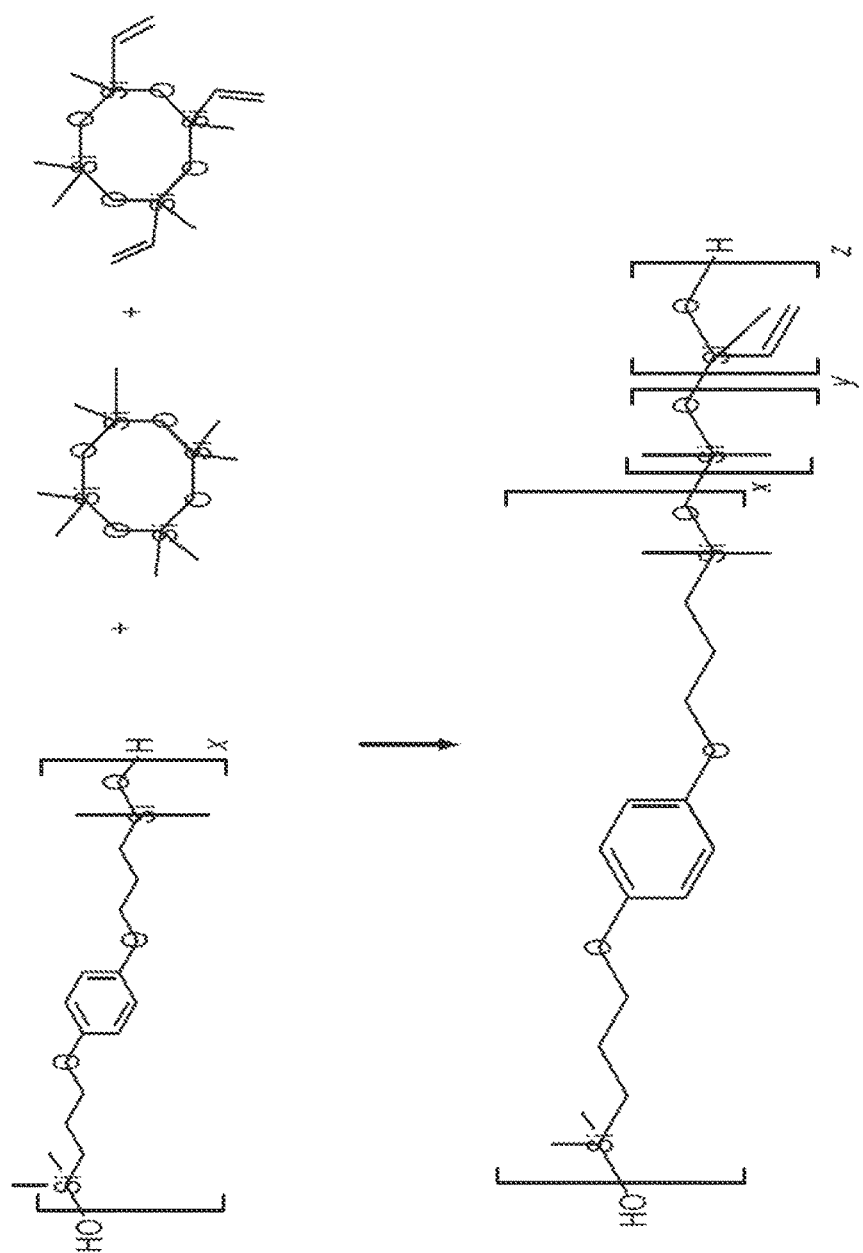
FIG. 3 depicts an alternative chemical equation for combining a siloxane polymer with one or more cyclic siloxanes to produce a siloxane copolymer with additional siloxane groups according to an embodiment.

In another embodiment, another preparation may involve a first synthesis step of combining a bis(bromomethyl) aromatic with an aliphatic vinyl alcohol under conditions that allow for nucleophilic substitution of the bromines by the aliphatic vinyl alcohol, as represented by the following equation:

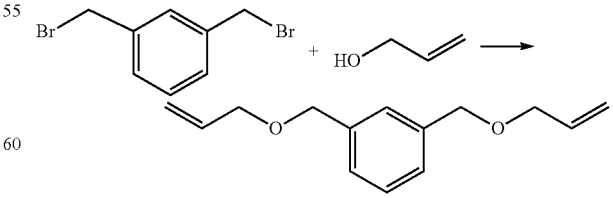

where the aliphatic vinyl alcohol is represented by allyl alcohol (prop-2-en-1-ol) and the bis(bromomethyl)aromatic is represented by alpha,alpha'1,4-dibromoxylenebenzene. In some embodiments, the resulting 1,4-bis(allyloxymethyl)

benzene may then be combined with a chlorosilane to form a bischlorosilane monomer, as represented by the following equation:

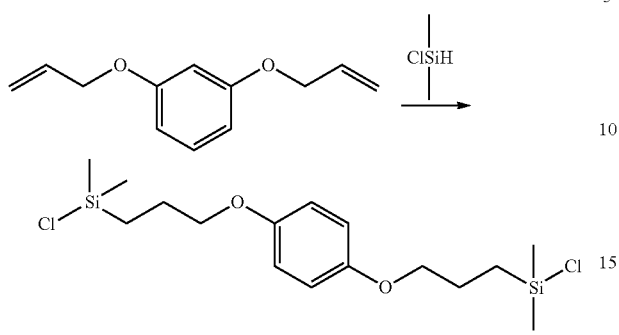

where the chlorosilane is represented by chlorodimethylsilane and the bischlorosilane monomer is 1,3-di(3-(chlorodimethylsilyl)propanoxymethyl)benzene. In some embodiments, the bischlorosilane monomer, in the presence of water, may undergo hydrolysis followed by condensation reactions to obtain a siloxane polymer, as represented by the following equation:

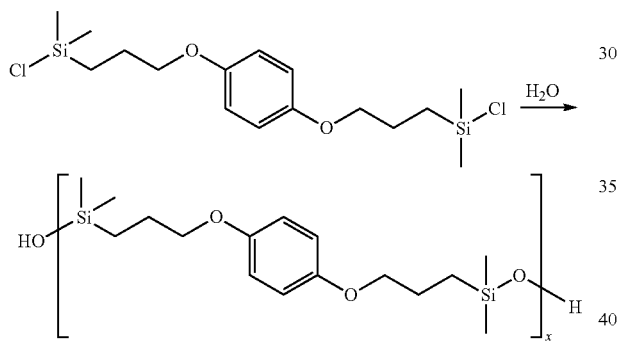

wherein x may be an integer from 1-200 and the siloxane polymer contains aromatic ethers. The siloxane polymer may then be combined with one or more cyclic siloxanes to produce a siloxane copolymer with additional siloxane groups, as represented by the equation depicted in FIG. 3. The siloxane polymer is the aromatic ether containing siloxane copolymer produced from the previous equation, and the cyclic siloxanes are represented by octamethylcyclotetrasiloxane and 1,3,5,7-tetravinyl-1,3,5,7-tetramethylcyclotetrasiloxane. In particular embodiments, the cyclic siloxanes may be in a solution comprising a ratio of about 1 part octamethylcyclotetrasiloxane to 4 parts 1,3,5,7-tetravinyl-1,3,5,7-tetramethylcyclotetrasiloxane by weight, wherein the octamethylcyclotetrasiloxane and 1,3,5,7-tetravinyl-1,3,5,7-tetramethylcyclotetrasiloxane, together, may be present in the solution at a concentration of about 80 percent by weight. In other embodiments, the copolymer may include m octamethylcyclotetrasiloxane repeating units and n 1,3,5,7-tetravinyl-1,3,5,7-tetramethylcyclotetrasiloxane repeating units, wherein m and n are each, independently, an integer greater than 4. In some embodiments, x, y, and z may each, independently, be integers from 1-1000. Scheme 4

In another embodiment, a preparation may involve a first synthesis step that includes combining an aromatic dicarboxylic acid with an aliphatic vinyl alcohol under conditions that allow for nucleophilic substitution of the carboxylic acids by the aliphatic vinyl alcohol, as represented by the following equation:

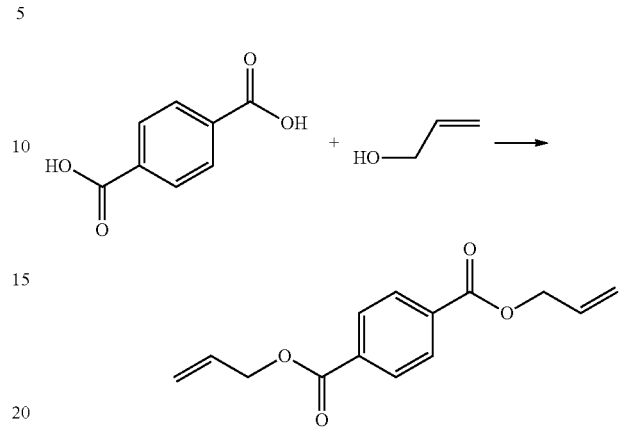

where the aliphatic vinyl alcohol is represented by allyl alcohol (prop-2-en-1-ol) and the dicarboxylic acid is represented by terephthalic acid. In some embodiments, the resulting diallyl terephthalate may then be combined with a chlorosilane to form a bischlorosilane monomer, as represented by the following equation:

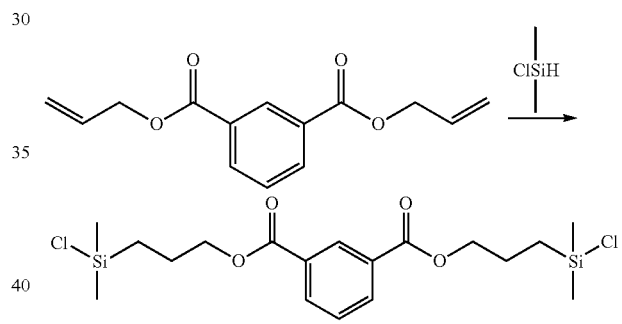

where the chlorosilane is represented by chlorodimethylsilane and the bischlorosilane monomer is di-3-chlorodimethylsilylpropyl terephthalate. In some embodiments, the bischlorosilane monomer, in the presence of water, may undergo hydrolysis followed by condensation reactions to obtain a siloxane polymer, as represented by the following equation:

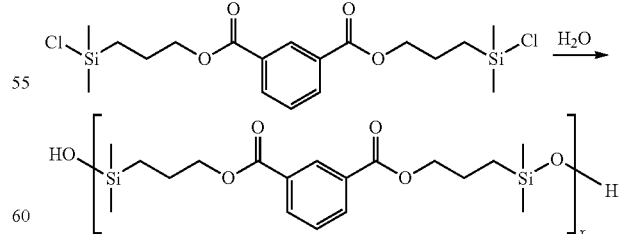

wherein x may be an integer from 1-200 and the siloxane polymer contains aromatic esters.

Figure 4:
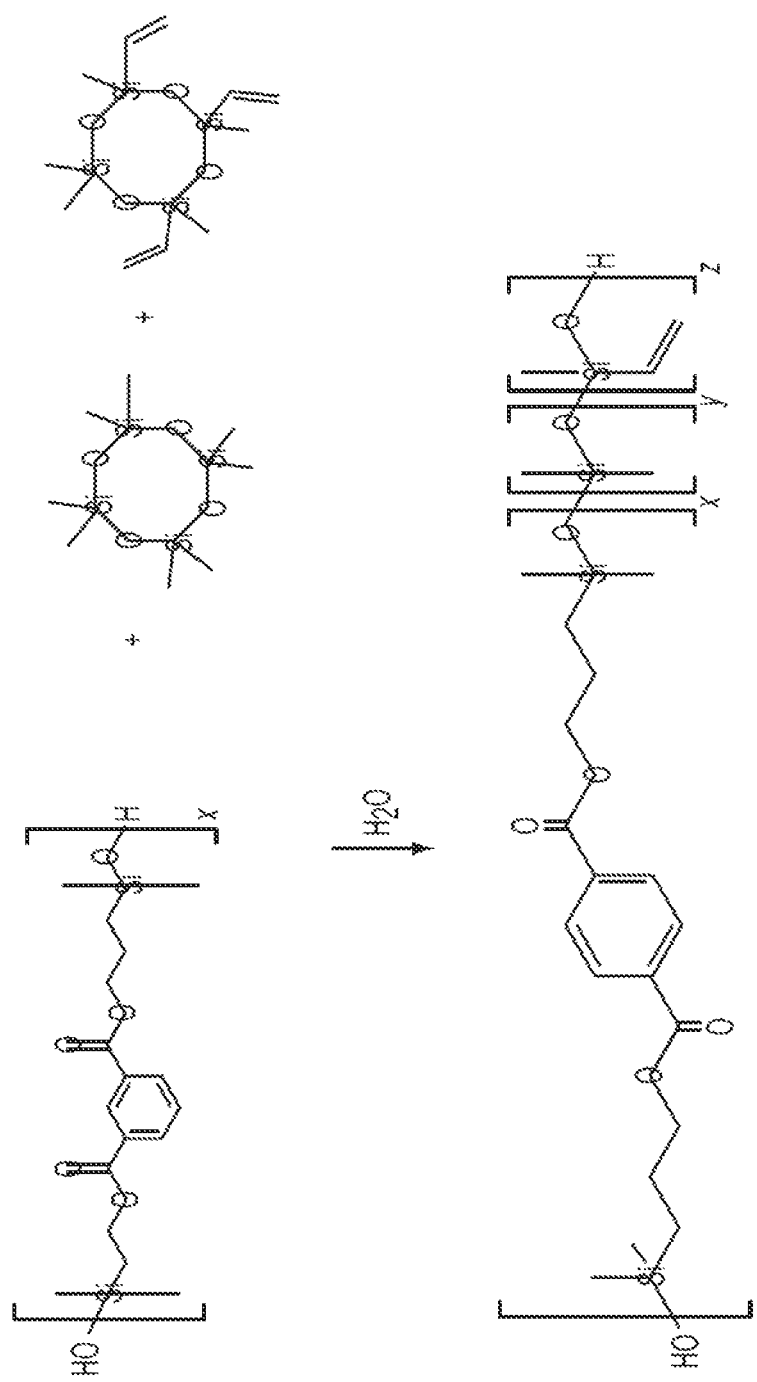
FIG. 4 depicts another alternative chemical equation for combining a siloxane polymer with one or more cyclic siloxanes to produce a siloxane copolymer with additional siloxane groups according to an embodiment.

The siloxane polymer may then be combined with one or more cyclic siloxanes to produce a siloxane copolymer with additional siloxane groups, as represented by the equation in FIG. 4. The siloxane polymer is the aromatic ester containing siloxane copolymer produced from the previous equation, and the cyclic siloxanes are represented by octamethylcyclotetrasiloxane and 1,3,5,7-tetravinyl-1,3,5,7-tetramethylcyclotetrasiloxane. In particular embodiments, the cyclic siloxanes may be in a solution comprising a ratio of about 1 part octamethylcyclotetrasiloxane to 4 parts 1,3,5,7-tetravinyl-1,3,5,7-tetramethylcyclotetrasiloxane by weight, wherein the octamethylcyclotetrasiloxane and 1,3,5,7-tetravinyl-1,3,5,7-tetramethylcyclotetrasiloxane, together, may be present in the solution at a concentration of about 80 percent by weight. In other embodiments, the copolymer may include m octamethylcyclotetrasiloxane repeating units and n 1,3,5,7-tetravinyl-1,3,5,7-tetramethylcyclotetrasiloxane repeating units, wherein m and n are each, independently, an integer greater than 4. In some embodiments, x, y, and z may each, independently, be integers from 1-1000.

Various experimental methods used to obtain the copolymers are described in the examples below.

EXAMPLES

Example 1

Copolymer Preparation

Reagents

Carbinol-terminated polydimethylsiloxanes were purchased from GELEST, Morrisville, Pa., and were used without further purification. Solvents such as toluene, tetrahydrofuran, and methanol at 99% purity were purchased from VWR, Radnor, Pa. and were used without further purification. DOWEX-50W-hydrogen acidic ion exchange resin and DRIERITE desiccant were also purchased from VWR.

Instrumentation

Size exclusion chromatography (SEC) was performed on a WATERS system that includes a WATERS HPLC 515 pump, a column temperature controller held at 35° C., a WATERS 2410 RI detector and two WATERS Styragel columns HT2 and HT5. The system was calibrated with narrow molecular weight styrene standards having a molecular weight range of 3,000 to 600,000 g/mol. Nuclear Magnetic Resonance (NMR) spectra were obtained on a Bruker Avance 400 MHz two-channel, multi-nuclear NMR spectrometer equipped with an Oxford magnet. Spectra for $^{13}C$ were collected with continuous proton decoupling. All NMR experiments were run in chloroform-d. Spectra were internally calibrated to either chloroform or tetramethylsilane. Fourier Transform Infrared (FTIR) spectra were collected on a PERKIN-ELMER Spectrum 400 FT-IR/FT-NIR spectrometer fitted with a universal Attenuated Total Reflectance (ATR) sampling accessory. All refractive indices were collected on a Milton Roy model 33.46.10 ABBE Refractometer at 20° C.

Copolymer Preparation

To prepare copolymers that include polydimethylsiloxane and methylene diisocyanate (PDMS-MDI copolymer), carbinol-terminated polydimethylsiloxane (10.00 g) having a molecular weight of 6460 g/mol (Gelest Inc., Morrisville, Pa.), toluene (100.0 mL) and a Teflon coated magnetic stir bar were added to a 250 mL three-neck round-bottomed flask. The flask was fitted with a Dean Stark trap attached a water cooled condenser, a gas inlet and a 100 mL pressure-equalizing dropper funnel. The flask was heated to 120.0° C. so that the toluene was brought to reflux. At least 10.0 mL was allowed to collect in the trap in order to remove water from the reaction apparatus. After this, the reaction mixture was cooled to 70.0° C. Then, the dropper funnel was charged with methylene diisocyanate (0.41 g) and tetrahydrofuran (4.0 mL). The reagents were rapidly added to the flask. The reaction progress was monitored by observing a crude sample by FTIR as well as SEC. The reaction was considered complete when the isocyanate peak at 2270 cm$^{-1}$ could no longer be observed with FTIR, which took approximately 2.00 hours. After this, the polymer was precipitated from a mixture of tetrahydrofuran and methanol three times, and then dried in a vacuum oven. This resulted in a colorless viscous oil having a Mw/Mn of 143,000/86,000 g/mol and a refractive index at 20° C. of 1.4129. IR v: 2962, 1732, 1540, 1413, 1257, 1072, 1008, 863, 785, 701,660 cm$^{-1}$.

To prepare copolymers that include polydimethylsiloxane and toluene diisocyanate (PDMS-TDI copolymer), carbinol-terminated polydimethylsiloxane (10.00 g) having a molecular weight of 6460 g/mol (Gelest Inc., Morrisville, Pa.), toluene (100.0 mL) and a Teflon coated magnetic stir bar were added to a 250 mL three-neck round-bottomed flask. The flask was fitted with a Dean Stark trap attached a water cooled condenser, a gas inlet and a 100 mL pressure-equalizing dropper funnel. The flask was heated to 120.0° C. so that the toluene was brought to reflux. At least 10.0 mL was allowed to collect in the trap in order to remove water from the reaction apparatus. After this, the reaction mixture was cooled to 70.0° C. Then, the dropper funnel was charged with toluene diisocyanate (0.27 g) and tetrahydrofuran (4.0 mL). These reagents were rapidly added to the flask. The reaction progress was monitored by observing a crude sample by FTIR as well as SEC. The reaction was considered complete when the isocyanate peak at 2270 cm$^{-1}$ could no longer be observed with FTIR, which took approximately 3.00 hours. After this, the polymer was precipitated from a mixture of tetrahydrofuran and methanol three times, and then dried in a vacuum oven. This resulted in a colorless viscous oil having a Mw/Mn of 195,000/128,000 g/mol and a refractive index at 20° C. of 1.4156. IR v: 2963, 1738, 1602, 1534, 1712, 1443, 1258, 1076, 1008, 864, 787, 701, 660 cm$^{-1}$.

To prepare copolymers that include polydimethylsiloxane and hydrogenated methylene diisocyanate (PDMS-HMDI copolymer), carbinol-terminated polydimethylsiloxane (10.00 g) having a molecular weight of 6460 g/mol (Gelest Inc., Morrisville, Pa.), toluene (100.0 mL) and a Teflon coated magnetic stir bar were added to a 250 mL three-neck round-bottomed flask. The flask was fitted with a Dean Stark trap attached a water cooled condenser, a gas inlet and a 100 mL pressure-equalizing dropper funnel. The flask was heated to 120.0° C. so that the toluene was brought to reflux. At least 10.0 mL was allowed to collect in the trap in order to remove water from the reaction apparatus. After this, the reaction mixture was cooled to 70.0° C. Then, the dropper funnel was charged with hydrogenated methylene diisocyanate (0.43 g) and tetrahydrofuran (4.0 mL). These reagents were rapidly added to the flask. The reaction progress was monitored by observing a crude sample by FTIR as well as SEC. The reaction was considered complete when the isocyanate peak at 2270 cm$^{-1}$ could no longer be observed with FTIR, which took approximately 20.0 hours. After this, the polymer was precipitated from a mixture of tetrahydrofuran and methanol three times, and then dried in a vacuum oven. This resulted in a colorless viscous oil having a Mw/Mn of 190,000/123,000 g/mol and a refractive index at 20° C. of 1.4164. IR v: 2963, 1728, 1707, 1528, 1445, 1413, 1258, 1078, 1009, 864, 785, 702, 661 cm$^{-1}$.

Example 2

Vinyl Functional Copolymer

Incorporation of methylvinylsiloxane units to a copolymer from Example 1 included adding DOWEX-50W-hydrogen acidic ion exchange resin (5.0 g) and a TEFLON coated magnetic stir bar to a 250 ml one-necked round-bottomed flask. The flask and its contents were dried for 4 hours at 100° C. under vacuum. After this time, 1,3,5,7-tetravinyl-1,3,5,7-tetramethylcyclotetrasiloxane (1.0 g), and a copolymer (100 g) as described in Example 1 were added to the flask. The flask was fitted with a drying tube (DRI-ERITE) and was heated to 70° C. The contents in the flask were maintained at this temperature for 8 hours, after which the crude product was diluted with THF (2:1 v,v solvent to polymer) and the DOWEX resin removed by filtration. The polymer was precipitated with methanol resulting in a viscous colorless polymer that includes methylvinylsiloxane repeat units within its backbone structure. The same procedure was repeated for each of the three copolymers PDMS-MDI, PDMS-TDI and PDMS-HMDI as described in Example 1 to form vinyl functional copolymers for use in Samples 3.1, 3.2 and 3.3, respectively, in Example 3 below.

Example 3

Two-Part Heat Curable Systems

A method of compounding vinyl functional copolymers with silica and poly(hydromethylsiloxane-co-dimethylsiloxane) crosslinker included the following: treated fumed silica (AEROSIL® R812 S from Evonik Corporation, NJ, USA or CAB-O-SIL® TS-530 from Cabot Corporation, MA, USA) may be compounded into a copolymer as described in Example 2 using a tangential sigma blade mixer. Table 1 below shows the silica loading that may be compounded into the copolymer from Example 2. Throughout mixing, the mixer's bowl was heated to 140° C. After an appropriate amount of silica in accordance with Table 1 had been added incrementally to the copolymer fluid, the resulting gum was mixed for at least 2 hours. As shown in Table 1, a cross-linking catalyst and a hydromethylsiloxane copolymer (cross-linker) were added to separate parts of the fumed silica/copolymer gum, thereby creating a two-part heat curable system made up of Parts A and B in Table 1. When Parts A and B are mixed together in equal portions, cured articles may be prepared using a heated press at 150° C. for five minutes, and further post curing the articles in a circulating air oven at 150° C. for 2 hours. The same procedure was repeated for each of the three copolymers from Example 2 to form Samples 3.1, 3.2 and 3.3 as described in Table 1 below.

TABLE 1

| | Sample 3.1 | | Sample 3.2 | | Sample 3.3 | |
|---|---|---|---|---|---|---|
| | Part A | Part B | Part A | Part B | Part A | Part B |
| Silica type | CAB-O-SIL® TS-530 | CAB-O-SIL® TS-530 | CAB-O-SIL® TS-530 | CAB-O-SIL® TS-530 | CAB-O-SIL® TS-530 | CAB-O-SIL® TS-530 |
| Silica loading [parts per hundred rubber (pphr)]* | 36 | 36 | 36 | 36 | 36 | 36 |
| Copolymer from Example 2 [parts by weight] | 88 | 96 | 88 | 96 | 88 | 96 |
| Poly(hydromethylsiloxane-co-dimethylsiloxane) (Si—H cross-linker) [parts by weight] | 12 | — | 12 | — | 12 | — |
| 5% Pt complex (platinum 1,3-divinyl-1,1,3,3-tetramethyldisiloxane) in xylenes (cross linking catalyst) [parts per hundred rubber (pphr)]* | — | 4 | — | 4 | — | 4 |

*Note:
"pphr" or "parts per hundred rubber" indicates parts of a component per hundred parts of the copolymer.

Example 4

Copolymer Preparation and Characterization

Instrumentation and Reagents

The instrumentation as described in Example 1 was used in Example 4. Polydimethylsiloxanes (PDMS) under the catalog names listed in Table 2 were purchased from GELEST INC., Morrisville, Pa. and were used without further purification. Solvents such as toluene, tetrahydrofuran, and methanol at 99% purity were purchased from VWR, Radnor, Pa. and were used without further purification.

Copolymer Preparation

Copolymers were prepared from combinations of aromatic monomers and polydimethylsiloxanes (PDMS) listed in Table 2. The first column provides label names of individual copolymers formed from each combination. The second column lists the aromatic monomer used in each combination. The third column shows the type of PDMS used in each combination. The fourth column lists the catalog name for the PDMS, which were purchased from GELEST INC., Morrisville, Pa. The final column lists the molecular weight of the PDMS.

TABLE 2

| Copolymer label | Aromatic Monomer | PDMS | GELEST catalog name for PDMS | PDMS molecular weight (g/mol) |
|---|---|---|---|---|
| MDI-SD1.0k | MDI | SD | DMS-C16 | 1000 |
| MDI-SD1.3k | (Methylene | (Hydroxyl | DMS-C15 | 1300 |
| MDI-SD6.4k | diisocyanate) | terminated | DMS-C21 | 6400 |

TABLE 2-continued

| Copolymer label | Aromatic Monomer | PDMS | GELEST catalog name for PDMS | PDMS molecular weight (g/mol) |
|---|---|---|---|---|
| MDI-SD16.6k | | PDMS) | DMS-C23 | 16,600 |
| TDI-SD1.0k | TDI | | DMS-C16 | 1000 |
| TDI-SD1.3k | (Toluene | | DMS-C15 | 1300 |
| TDI-SD6.4k | diisocyanate) | | DMS-C21 | 6400 |
| TDI-SD16.6k | | | DMS-C23 | 16,600 |
| HMDI-SD1.0k | HMDI | | DMS-C16 | 1000 |
| HMDI-SD1.3k | (Hydrogenated | | DMS-C15 | 1300 |
| HMDI-SD6.4k | methylene | | DMS-C21 | 6400 |
| HMDI-SD16.6k | diisocyanate) | | DMS-C23 | 16,600 |
| DAP-SH0.5k | DAP | SH | DMS-H03 | 500 |
| DAP-SH1.1k | (Diallyl | (Silicon-hydride | DMS-H11 | 1100 |
| DAP-SH4.5k | phthalate) | terminated | DMS-H21 | 4500 |
| DAP-SH20.8k | | PDMS) | DMS-H25 | 20,800 |

TABLE 2-continued

| Copolymer label | Aromatic Monomer | PDMS | GELEST catalog name for PDMS | PDMS molecular weight (g/mol) |
|---|---|---|---|---|
| DIP-SH0.5k | DIP | | DMS-H03 | 500 |
| DIP-SH1.1k | (Diallyl | | DMS-H11 | 1100 |
| DIP-SH4.5k | isophthalate) | | DMS-H21 | 4500 |
| DIP-SH20.8k | | | DMS-H25 | 20,800 |
| DOB-SH0.5k | DOB | | DMS-H03 | 500 |
| DOB-SH1.1k | (Diallyloxy benzene) | | DMS-H11 | 1100 |

The chemical formulas of MDI, TDI, HMDI and SD listed in Table 2 are as follows:

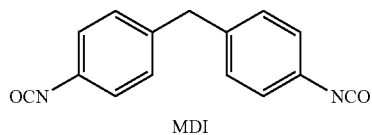
MDI

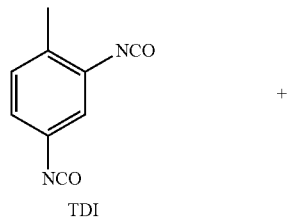
TDI

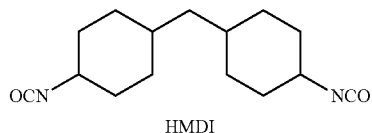
HMDI

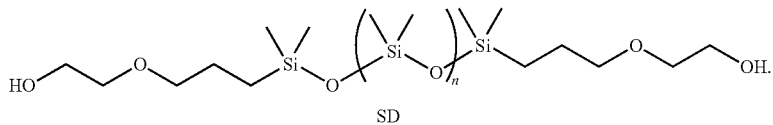
SD

The chemical formulas of DAP, DIP, DOB and SH listed in Table 2 are as follows:

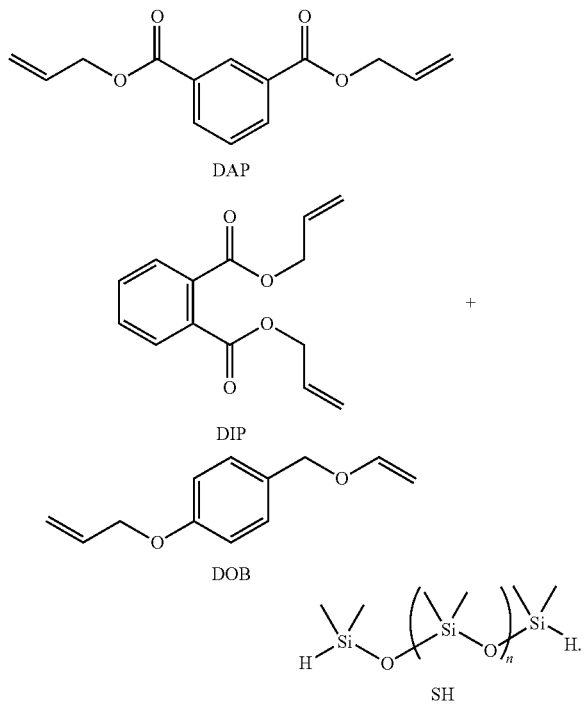

To prepare a copolymer formed from SD and a diisocyanate, and using copolymer MDI-SD1.0k as an example, carbinol-terminated polydimethylsiloxane (1.50 mmol) having the molecular weight 1000 g/mol, toluene (100.0 mL) and a Teflon coated magnetic stir bar were added to a 250 mL three-neck round-bottomed flask. The flask was fitted with a Dean Stark trap attached a water cooled condenser, a gas inlet and a 100 mL pressure-equalizing dropper funnel. The flask was heated to 120.0° C. so that the toluene was brought to reflux. At least 10.0 mL was allowed to collect in the trap in order to remove water from the reaction apparatus. After this, the reaction mixture was cooled to 70.0° C. Then, the dropper funnel was charged with methylene diisocyanate (1.60 mmol) and tetrahydrofuran (4.0 mL). These reagents were added to the flask over a period of 1.0 minute, followed by two drops of dibutyltin dilaurate catalyst (Dabco T-12 from Air Products and Chemicals, Inc., Allentown, Pa.). The reaction progress was monitored by observing a crude sample by FTIR as well as SEC. The reaction was considered complete when the isocyanate peak at 2270 cm$^{-1}$ could no longer be observed with FTIR (approximately 2 hours). After this, the polymer was precipitated from a mixture of tetrahydrofuran and methanol three times, and then dried in a vacuum oven. This resulted in a colorless gum. The same steps were repeated to prepare the remaining copolymers that combined SD with MDI, TDI or HMDI using the respective combinations of reagents listed in Table 2. Yields of the copolymers after precipitation ranged from 70% to 85%.

To prepare a copolymer formed from SH and a diallyl monomer, and using copolymer DOB-SH0.5k as an example, hydride-terminated polydimethylsiloxane (3.30 mmol) having the molecular weight 500 g/mol, toluene (100.0 mL) and a Teflon coated magnetic stir bar were added to a 250 mL three-neck round-bottomed flask. The flask was fitted with a Dean Stark trap attached a water cooled condenser, a gas inlet and a 100 mL pressure-equalizing dropper funnel. The flask was heated to 140.0° C. so that the toluene was brought to reflux. At least 5.0 mL was allowed to collect into the trap in order to remove water from the reaction apparatus. After this, the reaction mixture was cooled to 120.0° C. Then, the dropper funnel was charged with diallyloxy benzene (3.30 mmol) and tetrahydrofuran (4.0 mL). These reagents were added to the flask over a period of 1 minute, followed by three drops of platinum-divinyltetramethyldisiloxane complex. The reaction progress was monitored by observing a crude sample by FTIR as well as SEC. The reaction was considered complete when the silane peak at 2108 cm$^{-1}$ could no longer be observed with FTIR (approximately 4 hours). After this, the polymer was precipitated from a mixture of tetrahydrofuran and methanol three times, and then dried in a vacuum oven. This resulted in a slightly brown gum due to the presence of residual catalyst. To remove the residual catalyst, the polymer was passed through a packed column of silica gel to result in a colorless gum. The same steps were repeated to prepare the remaining copolymers that combined SH with DAP, DIP or DOB using the respective combinations of reagents listed in Table 2. Yields of the copolymers after precipitation ranged from 70% to 85%.

Characterization Data

Characterization data for each of the copolymers prepared in this Example is provided below.

MDI-SD1.0k: Mw/Mn: 26,600/16,100. $^1$H NMR (400 MHz, CDCl$_3$): δ 7.29 (d, J=7.4 Hz, 4H), 7.09 (d, J=7.8 Hz, 4H), 6.60 (s, 2H), 4.10 (t, J=6.9 Hz, 4H), 3.88 (s, 2H), 1.69 (m, 4H), 0.57 (m, 4H), 0.23 to −0.090 (s, 120 H). $^{13}$C NMR (400 MHz, CDCl$_3$): δ 154.06, 136.38, 136.22, 129.54, 119.04, 67.71, 40.75, 22.99, 14.11, 2.49 to −0.096. IR (v): 3323, 2962, 2901, 1709, 1598, 1526, 1414, 1310, 1258, 1222, 1070, 1014, 861, 790, 703 cm$^{-1}$, RI (20° C.): 1.463.

MDI-SD1.3k: Mw/Mn: 167,000/117,000. $^1$H NMR (400 MHz, CDCl$_3$): δ 7.27 (d, J=8.4 Hz, 4H), 7.09 (d, J=7.8 Hz, 4H), 6.71 (s, 2 H), 4.30 (t, J=4.1 Hz, 4H), 3.87 (s, 2H), 3.66 (t, J=4.3 Hz, 4H), 3.44 (J=7.0 Hz, 4H), 1.63 (m, 4H), 0.53 (m, 4H), 0.20 to −0.078 (s, 100H). $^{13}$C NMR (400 MHz, CDCl$_3$): 153.43, 136.32, 135.83, 129.44, 118.88, 74.21, 68.84, 64.31, 40.55, 23.35, 14.06, 1.24-0.061. IR (v): 3324, 2962, 2890, 1736, 1713, 1599, 1533, 1439, 1413, 1311, 1257, 1222, 1068, 1011, 861, 838, 787, 702 cm$^{-1}$. RI (20° C.): 1.459.

MDI-SD6.4k: Mw/Mn: 143,000/86,000. $^1$H NMR (400 MHz, CDCl$_3$): δ 7.28 (d, J=7.7 Hz, 4H), 7.09 (d, J=8.2 Hz, 4H), 6.69 (s, 2H), 4.31 (t, J=4.6 Hz, 4H), 3.88 (s, 2H), 3.67 (t, J=4.7 Hz, 4H), 3.45 (J=6.9 Hz, 4H), 1.64 (m, 4H), 0.53 (m, 4H), 0.13 to 0.02 (s, 500-700H). $^{13}$C NMR (400 MHz, CDCl$_3$): δ 153.61, 136.52, 136.09, 129.44, 119.05, 74.46, 69.06, 64.56, 40.82, 23.55, 14.35, 2.40-0.14. IR (v): 2962, 2906, 1423, 1257, 1085, 1008, 875, 792, 750, 710 cm$^{-1}$, RI (20° C.): 1.413.

MDI-SD16.6k: Mw/Mn: 135,000, 89,000. $^1$H NMR (400 MHz, CDCl$_3$): δ 7.28 (d, J=8.5 Hz, 4H), 7.12 (d, J=8.3 Hz, 4H), 6.65 (s, 2H), 4.31 (t, J=4.6 Hz, 4H), 3.88 (s, 2H), 3.66 (t, J=4.6 Hz, 4H), 3.44 (t, J=7.1 Hz, 4H), 1.63 (m, 4H), 0.53 (m, 4H), 0.018 to −0.125 (s, 1200-1400H). $^{13}$C NMR (400 MHz, CDCl$_3$): δ 153.61, 136.57, 136.08, 129.65, 119.04, 74.43, 69.06, 64.54, 40.76, 23.56, 14.26, 1.33-1.17. IR (v): 2963, 2906, 1738, 1601, 1537, 1413, 1258, 1072, 1010, 864, 793, 702, 661 cm$^{-1}$, RI (20° C.): 1.411.

TDI-SD1.0k: Mw/Mn: 133,000/46,500. $^1$H NMR (400 MHz, CDCl$_3$): δ 7.78 (br s, 2H, N—H), 7.25 (br d, isomer), 7.07 (d, J=8.1 Hz, 2H), 6.68 (br s, isomer), 6.42 (br s, 1H), 4.11 (m, 4H), 2.19 (s, 3H), 1.69 (m, 4H), 0.57 (m, 4H), 0.22 to −0.069 (s, 120H). $^{13}$C NMR (400 MHz, CDCl$_3$): δ 153.72, 136.83, 136.31, 130.74, 114.17, 110.89, 68.75-66.65, 22.88, 16.70, 13.97, 1.84 to −0.25. IR (v): 3314, 2962, 2910, 1709, 1600, 1533, 1449, 1414, 1257, 1223, 1071, 1013, 863, 837, 792, 702, 663 cm$^{-1}$, RI (20° C.): 1.462.

TDI-SD1.3k: Mw/Mn: 218,000/147,000. $^1$H NMR (400 MHz, CDCl$_3$): δ 7.77 (br s), 7.23 (br d, isomer), 7.08 (br d), 6.61 (br s, isomer), 6.40 (br s), 4.11 (m), 3.60 (m), 3.45 (m), 2.18 (s), 1.63 (m), 0.54 (m), 0.30 to −0.27 (s, 100H). $^{13}$C NMR (400 MHz, CDCl$_3$): δ 153.95, 137.00, 136.51, 131.026, 69.20-66.45, 29.81, 26.58, 23.03, 17.07, 14.15. IR (v): 3324, 2962, 2910, 1737, 1603, 1536, 1450, 1415, 1260, 1227, 1076, 1023, 875, 798, 701, 667 cm$^{-1}$, RI (20° C.): 1.448.

TDI-SD6.4k: Mw/Mn: 195,000/128,000. $^1$H NMR (400 MHz, CDCl$_3$): δ 7.84 (br s), 7.19 (br d), 7.07 (d, J=8.6 Hz), 6.69 (br s), 6.52 (br s), 4.32 (m), 3.67 (m), 3.45 (m), 2.18 (s), 1.63 (m), 0.54 (m), 0.26 to −0.11 (s, 700-900H). $^{13}$C NMR (400 MHz, CDCl$_3$): δ 153.58, 136.82, 136.46, 136.27, 130.97, 121.68, 114.27, 111.03, 74.38, 69.05, 64.54, 23.53, 17.39, 14.33, 3.18 to −0.844. IR (v): 2963, 2906, 1738, 1604, 1536, 1447, 1413, 1258, 1091, 1009, 864, 790, 701, 686, 661 cm$^{-1}$, RI (20° C.): 1.416.

TDI-SD16.6k: Mw/Mn: 92,900/53,500. $^1$H NMR (400 MHz, CDCl$_3$): δ 7.85 (br s), 7.20 (br d), 7.06 (d, J=8.6 Hz), 6.75 (br s), 6.53 (br s), 4.31 (m), 3.68 (m), 3.45 (m), 2.18 (s), 1.63 (m), 0.53 (m), 0.21 to −0.11 (s, 1500-2000H). $^{13}$C NMR (400 MHz, CDCl$_3$): δ 151.08, 136.56, 131.07, 71.82, 69.56, 62.13, 23.55, 14.35, 3.37 to −0.178. IR (v): 2963, 2906, 1739, 1604, 1536, 1448, 1413, 1258, 1079, 1009, 864, 788, 701, 660 cm$^{-1}$, RI (20° C.): 1.408.

HMDI-SD1.0k: Mw/Mn: 43,900/24,600. $^1$H NMR (400 MHz, CDCl$_3$): δ 7.23-7.12 (s, 0.2H), 4.76 (s, 1H), 4.51 (s, 1H), 3.96 (br t, 4H), 3.73 (m, 2H), 1.96 (d, J=10.53 Hz, 2H), 1.74-1.46 (m, 16H), 1.40 (m, 2H) 1.22 (m, 2H), 1.16-0.834 (m, 10H), 0.512 (m, 4H), 0.191 to −0.104 (s, 100H) $^{13}$C NMR (400 MHz, CDCl$_3$): δ 156.12, 68.72-65.18, 50.93-49.93, 47.82-46.18, 44.29-42.83, 34.45-31.47, 30.68-27.34, 26.72, 23.14, 14.37-13.86, 2.53 to −0.92. IR (v): 3331, 2961, 2930, 1697, 1529, 1450, 1412, 1321, 1257, 1014, 863, 837, 790, 702, 664 cm$^{-1}$, RI (20° C.): 1.4461.

HMDI-SD1.3k: Mw/Mn: 85,800/50,000. $^1$H NMR (400 MHz, CDCl$_3$): δ 6.99 (s), 4.92 (br d), 4.62 (br d), 4.19 (m), 3.77 (s), 3.60 (m), 3.42 (m), 1.98 (br d), 1.75-1.49 (m), 1.41 (m), 1.24 (m), 1.14-0.87 (m), 0.52 (m), 0.14 to −0.052 (100H). $^{13}$C NMR (400 MHz, CDCl$_3$): δ 155.72, 74.35, 69.19, 64.02, 50.46, 47.07, 43.36, 34.64-27.05, 23.50, 14.14, 2.35 to −0.390. IR (v): 3336, 2962, 2931, 2857, 1706, 1528, 1450, 1413, 1319, 1258, 1087, 1013, 862, 790, 701, 663 cm$^{-1}$, RI (20° C.): 1.4435.

HMDI-SD6.4k: Mw/Mn: 190,000/123,000. $^1$H NMR (400 MHz, CDCl$_3$): δ 6.97 (s, 2H), 4.90 (br d, 1H), 4.61 (br d, 1H), 4.20 (m, 4H), 3.73 (m), 3.61 (m, 4H), 3.42 (m, 4H), 1.99 (br d, 2H), 1.75-1.50 (m, 16H), 1.42 (m), 1.25 (m), 1.15-0.87 (m), 0.52 (m), 0.130 to −0.010 (s, 500-700H). $^{13}$C NMR (400 MHz, CDCl$_3$): δ 155.82, 74.37, 69.30, 64.03, 50.49, 47.42, 43.55 34.74-27.40, 23.54, 14.25, 2.31-0.189. IR (v): 2963, 2910, 1706, 1528, 1448, 1413, 1258, 1079, 1009, 864, 793, 702, 703, 661 cm$^{-1}$, RI (20° C.): 1.4164.

HMDI-SD16.6k: Mw/Mn: 146,000/77,400. $^1$H NMR (400 MHz, CDCl$_3$): δ 6.98 (s, 2H), 4.91 (br d, 1H), 4.60 (br d, 1H), 4.20 (m, 4H), 3.73 (m), 3.61 (m, 4H), 3.43 (m, 4H), 1.98 (br d), 1.75-1.49 (m), 1.38 (m), 1.29 (m), 1.07 (m), 0.89 (m), 0.52 (m, 4H), 0.238 to −0.069 (s, 2000H). $^{13}$C NMR (400 MHz, CDCl$_3$): δ 155.74, 74.38, 69.37, 63.88, 50.49, 47,42, 43.55, 34.82-21.70, 15.62-12.87, 5.56 to −1.22. IR (v): 2963, 2858, 1727, 1413, 1258, 1070, 1011, 864, 792, 703, 661 cm$^{-1}$, RI (20° C.): 1.4114.

DAP-SH0.5k: Mw/Mn: 5,360/2,950. $^1$H NMR (400 MHz, CDCl$_3$): δ 7.73 (m, 2H), 7.53 (m, 2H), 4.80 (d, J=6.30 Hz, 2H), 4.26 (m, 4H), 1.76 (m, 4H), 0.61 (m, 4H), 0.218 to −0.092 (s, 150H). $^{13}$C NMR (400 MHz, CDCl$_3$): δ 167.68, 132.65-128.78, 68.4, 22.72, 14.16, 2.54 to −0.046. IR (v): 2962, 2905, 1732, 1555, 1581, 1448, 1413, 1257, 1079, 1013, 863, 792, 744, 703 cm$^{-1}$, RI (20° C.): 1.4314.

DAP-SH1.1k: Mw/Mn: 11,900/8,050. $^1$H NMR (400 MHz, CDCl$_3$): δ 7.72 (m, 2H), 7.52 (m, 2H), 4.80 (d, J=5.75Hz, 2H), 4.27 (m, 4H), 1.77 (m, 4H), 0.61 (m, 4H), 0.244 to −0.090 (s, 650H). $^{13}$C NMR (400 MHz, CDCl$_3$): δ 167.88, 132.69-128.81, 68.44, 22.75, 14.36, 3.06 to −0.010. IR (v): 2963, 2906, 1733, 1413, 1258, 1080, 1011, 864, 793, 701, 662 cm$^{-1}$, RI (20° C.): 1.4220.

DAP-SH4.5k: Mw/Mn: 63,800/39,100. $^1$H NMR (400 MHz, CDCl$_3$): δ 7.73 (m, 2H), 7.53 (m, 2H), 4.80 (d, J=6.30 Hz, 2H), 4.26 (m, 4H), 1.76 (m, 4H), 0.61 (m, 4H), 0.218 to −0.092 (s, 4,000H). $^{13}$C NMR (400 MHz, CDCl$_3$): δ 167.64, 13.25-127.76, 68.35, 30.80-28.67?, 22.44, 14.03, 4.43 to −1.06. IR (v): 2963, 2906, 1734, 1448, 1412, 1258, 1079, 1009, 863, 790, 702, 686, 660 cm$^{-1}$, RI (20° C.): 1.409.

DAP-SH20.8k: Mw/Mn: 254,000/91,300. $^1$H NMR (400 MHz, CDCl$_3$): δ $^1$H NMR (400 MHz, CDCl$_3$): δ 7.73 (m, 2H), 7.53 (m, 2H), 4.80 (d, J=6.30 Hz, 2H), 4.26 (m, 4H), 1.76 (m, 4H), 0.61 (m, 4H), 0.218 to −0.092 (s, 10,000H). $^{13}$C NMR (400 MHz, CDCl$_3$): δ 167.64, 13.25-127.76, 68.35, 30.80-28.67?, 22.44, 14.03, 4.43 to −1.06. IR (v): 2963, 2906, 1733, 1413, 1258, 1080, 1011, 864, 790, 702, 661 cm$^{-1}$, RI (20° C.): 1.407.

DIP-SH0.5k: Mw/Mn: 2,280/1,170. $^1$H NMR (400 MHz, CDCl$_3$): δ 8.80 (s, 1H), 8.73 (s, 1H), 8.32 (d, J=7.8 Hz, 2H), 8.25 (d, J=7.8 Hz, 2H), 7.60 (t, J=7.6 Hz, 1H), 7.55 (t, J=7.9 Hz, 1H), 4.32 (m, 4H), 1.83 (m, 2H), 0.64 (m, 2H), 0.23 to −0.021 (s, 100H). $^{13}$C NMR (400 MHz, CDCl$_3$): δ 165.91, 134.92-133.45, 131.69-128.14, 67.92, 22.89, 14.33, 2.38-0.123. IR (v): 2962, 2904, 1728, 1703, 1610, 1413, 1300, 1258, 1081, 1017, 730, 793, 700 cm$^{-1}$, RI (20° C.): 1.4371.

DIP-SH1.1k: Mw/Mn: 37,700/9,560. $^1$H NMR (400 MHz, CDCl$_3$): δ 8.78 (s, 1H), 8.71 (s, 1H), 8.30 (d, J=7.8 Hz, 2H), 8.23 (d, J=7.8 Hz, 2H), 7.58 (t, J=7.6 Hz, 1H), 7.53 (t, J=7.9 Hz, 1H), 4.32 (m, 4H), 1.822 (m, 2H), 1.37 (m, 2H), 0.637 (m, 2H), 0.54 (m, 2H), 0.145 to 0.023 (s, 400H). $^{13}$C NMR (400 MHz, CDCl$_3$): δ 166.07, 165.85, 134.87-133.69, 131.53-130.95, 129.91, 129.07, 128.82, 128.60, 68.13, 22.94, 21.10, 18.33, 16.95, 14.30, 1.67-0.029. IR (v): 2963, 2905, 1730, 1703, 1413, 1301, 1258, 1188, 1010, 863, 791, 731, 700, 662 cm$^{-1}$, RI (20° C.): 1.418.

DIP-SH4.5k: Mw/Mn: 102,000/69,100. $^1$H NMR (400 MHz, CDCl$_3$): δ8.78 (s, 1H), 8.71 (s, 1H), 8.30 (d, J=7.8 Hz, 2H), 8.23 (d, J=7.8 Hz, 2H), 7.58 (t, J=7.6 Hz, 1H), 7.53 (t, J=7.9 Hz, 1H), 4.32 (m, 4H), 1.822 (m, 2H), 1.37 (m, 2H), 0.637 (m, 2H), 0.54 (m, 2H), 0.145 to 0.023 (s, 3,000H). $^{13}$C NMR (400 MHz, CDCl$_3$): δ 166.07, 134.43, 131.43, 128.92, 115.69??, 68.85-67.52, 25.85, 22.96, 14.33, 2.49 to −0.153. IR (v): 2963, 2898, 1731, 1413, 1258, 1089, 1009, 864, 788, 701, 661 cm$^{-1}$, RI (20° C.): 1.4091.

DIP-SH20.8k: Mw/Mn: 139,000/93,100. $^1$H NMR (400 MHz, CDCl$_3$): δ 8.78 (s, 1H), 8.71 (s, 1H), 8.30 (d, J=7.8 Hz, 2H), 8.23 (d, J=7.8 Hz, 2H), 7.58 (t, J=7.6 Hz, 1H), 7.53 (t, J=7.9 Hz, 1H), 4.32 (m, 4H),1.822 (m, 2H), 1.37 (m, 2H), 0.637 (m, 2H), 0.54 (m, 2H), 0.145 to 0.023 (s, 10,000H).

$^{13}$C NMR (400 MHz, CDCl$_3$): δ 166.07, 134.43, 131.43, 128.92, 68.85-67.52, 25.85, 22.96, 14.33, 2.49 to −0.153. IR (v): 2963, 2907, 1413, 1258, 1090, 1009, 864, 792, 701, 661 cm$^{-1}$, RI (20° C.): 1.4068.

DOB-SH0.5k: Mw/Mn: 18,700/7,360. $^1$H NMR (400 MHz, CDCl$_3$): δ 6.82 (s, 4H), 3.86 (t, J=6.7 Hz, 4H), 1.80 (m, 4H), 0.65 (m, 4H), 0.244 to −0.077 (s, 140H). $^{13}$C NMR (400 MHz, CDCl$_3$): δ 153.27, 115.60, 115.40, 71.26, 23.47, 14.27, 2.16 to 0.23. IR (v): 2961, 1507, 1470, 1412, 1258, 1227, 1012, 789, 703 cm$^{-1}$, RI (20° C.): 1.448.

DOB-SH1.1k: Mw/Mn: 37,800/22,600. $^1$H NMR (400 MHz, CDCl$_3$): δ 6.84 (m, 4H), 3.87 (t, J=6.8 Hz, 4H), 1.80 (m, 4H), 0.65 (m, 4H), 0.244 to −0.077 (s, 600-700H). $^{13}$C NMR (400 MHz, CDCl$_3$): δ 153.65, 116.04-115.38, 71.16, 23.54, 14.34, 2.72 to −0.19. IR (v): 2963, 1508, 1413, 1258, 1079, 1010, 864, 789, 729 cm$^{-1}$, RI (20° C.): 1.417.

Results and Discussion

The weight-average molecular weight ($M_w$), number-average molecular weight ($M_n$), aromatic ring content and refractive index value of each of the copolymers prepared in this Example are provided in Table 3. The aromatic ring content and refractive index of a conventional silicone material, Poly(dimethyl-co-diphenylsiloxane) (PDMDPS), were obtained from the reference, Cristina Eliza Brunchi, Anca Filimon, Maria Cazacu, and Silvia Ioan, "Properties of Some Poly(siloxane)s for Optical Applications High Performance Polymers", 21: 31-47 (Mar. 4, 2008).

TABLE 3

| Copolymer | $M_w$ (g/mol × 1000) | $M_n$ (g/mol × 1000) | Phenyl content (mass %) | Refractive index at 20° C. |
|---|---|---|---|---|
| MDI-SD1.0k | 26.6 | 16.1 | 11.68 | 1.470 |
| MDI-SD1.3k | 167 | 117 | 9.39 | 1.459 |
| MDI-SD6.4k | 143 | 86.0 | 2.27 | 1.413 |
| MDI-SD16.6k | 135 | 89.0 | 0.90 | 1.411 |
| TDI-SD1.0k | 133 | 46.5 | 6.12 | 1.462 |
| TDI-SD1.3k | 218 | 147 | 4.86 | 1.448 |
| TDI-SD6.4k | 195 | 128 | 1.13 | 1.416 |
| TDI-SD16.6k | 92.9 | 53.5 | 0.45 | 1.408 |
| HMDI-SD1.0k | 43.9 | 24.6 | 12.19 | 1.446 |
| HMDI-SD1.3k | 85.8 | 50.0 | 9.82 | 1.444 |
| HMDI-SD6.4k | 190 | 123 | 2.38 | 1.416 |
| HMDI-SD16.6k | 146 | 77.4 | 0.95 | 1.411 |
| DAP-SH0.5k | 5.36 | 2.95 | 9.16 | 1.431 |
| DAP-SH1.1k | 11.9 | 8.05 | 5.27 | 1.422 |
| DAP-SH4.5k | 63.8 | 39.1 | 1.56 | 1.409 |
| DAP-SH20.8k | 254 | 91.3 | 0.36 | 1.407 |
| DIP-SH0.5k | 2.28 | 1.17 | 9.16 | 1.437 |
| DIP-SH1.1k | 37.7 | 9.56 | 5.27 | 1.418 |
| DIP-SH4.5k | 102 | 69.1 | 1.56 | 1.409 |
| DIP-SH20.8k | 139 | 93.1 | 0.36 | 1.407 |
| DOB-SH0.5k | 18.7 | 7.36 | 9.82 | 1.448 |
| DOB-SH1.1k | 37.8 | 22.6 | 5.49 | 1.417 |
| PDMDPS | | | 33.00 | 1.440 |
| PDMDPS | | | 21.32 | 1.425 |
| PDMDPS | | | 12.55 | 1.413 |
| PDMDPS | | | 8.08 | 1.408 |

Figure 5:
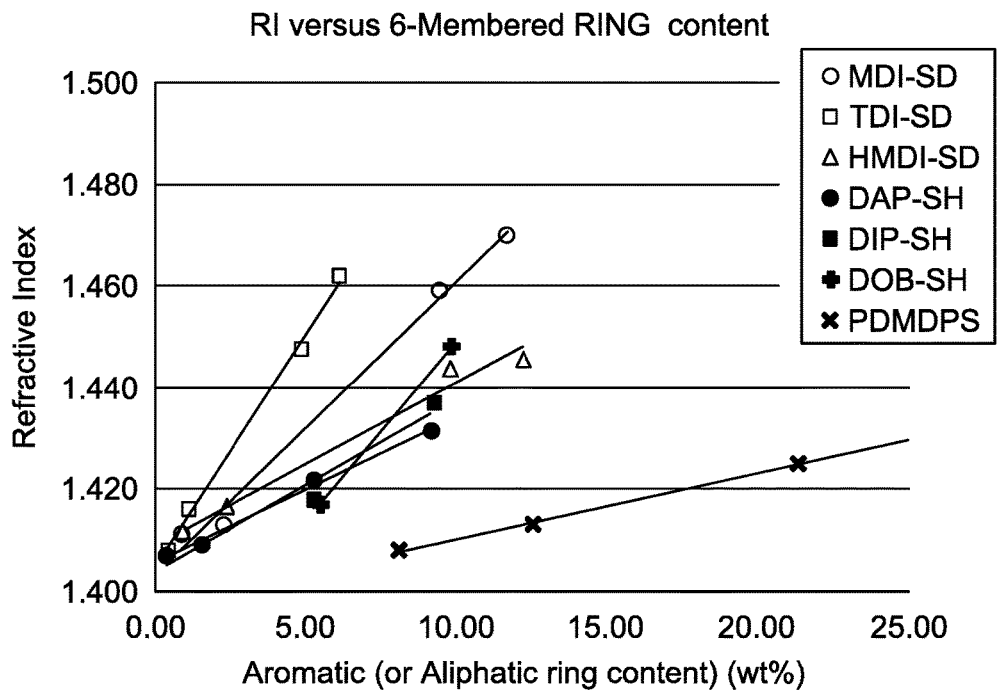
FIG. 5 depicts a graph of refractive index values versus aromatic content for copolymers formed in accordance with some embodiments, and poly(dimethyl-co-diphenylsiloxane) (PDMDPS).

A graph of refractive index (RI) values plotted versus the aromatic ring content, or aliphatic ring content in the case of HMDI, for all series of copolymers prepared in this Example is shown in FIG. 5. In FIG. 5, the unfilled round symbol "○" represents the MDI-SD series of copolymers, the unfilled square symbol "□" represents the TDI-SD series of copolymers, the unfilled triangle symbol "Δ" represents the HMDI-SD series of copolymers, the filled round symbol "●" represents the DAP-SH series of copolymers, the filled square symbol "■" represents the DIP-SH series of copolymers, the plus symbol "+" represents the DOB-SH series of copolymers, and the cross symbol "x" represents the PDMDPS copolymer. It can be noted from FIG. 5 that the TDI-SD series of copolymers exhibited the highest RI values, followed by the copolymers from the MDI-SD series. Both series of copolymers include an electron rich amide unit adjacent to the aromatic ring, which could suggest that donation of additional electron density into the ring by the amide unit may increase polarizability, and in turn increase refractive index of the material. It can also be noted from FIG. 5 that the PDMDPS material exhibited the lowest RI values.

The phthalate based copolymers (DAP-SH and DIP-SH series) have an ester linkage adjacent to the aromatic ring. Their RI values have shown to be lower than those of the TDI-SD and MDI-SD series but higher than those of PDMDPS. The phthalate based copolymers have ester groups, which are electron withdrawing, and hence may not increase the electron density of the aromatic ring. Without being bound by theory, the lower electron density in the aromatic rings of the phthalate based copolymers due to the electron withdrawing ester groups, could contribute to the lower RI values of the phthalate based copolymers as compared to the copolymers of the TDI-SD and MDI-SD series.

The HMDI-SD series of copolymers do not possess any aromatic content, but instead have fully saturated ring structures. The RI values of the HMDI-SD series of copolymers are similar to those measured for the phthalate based copolymers, but are still higher than the RI values for PDMDPS.

The diallyloxy benzene series of copolymers (DOB-SH), have an ether linkage adjacent to the aromatic ring. The copolymers in the series displayed higher RI values as compared to PDMDPS, but exhibited lower RI values than those of the TDI-SD and MDI-SD series. Hence, it can be observed that by introducing an aliphatic cyclic or aromatic ring containing groups into the PDMS backbone, RI values of the resulting copolymers may be increased as compared to the PDMDPS material. In addition, by introducing electron donating units, such as amide units, adjacent to the aromatic ring to couple the aromatic ring to the PDMS, the RI values of the resulting copolymers can be further increased or optimized.

Figure 6:
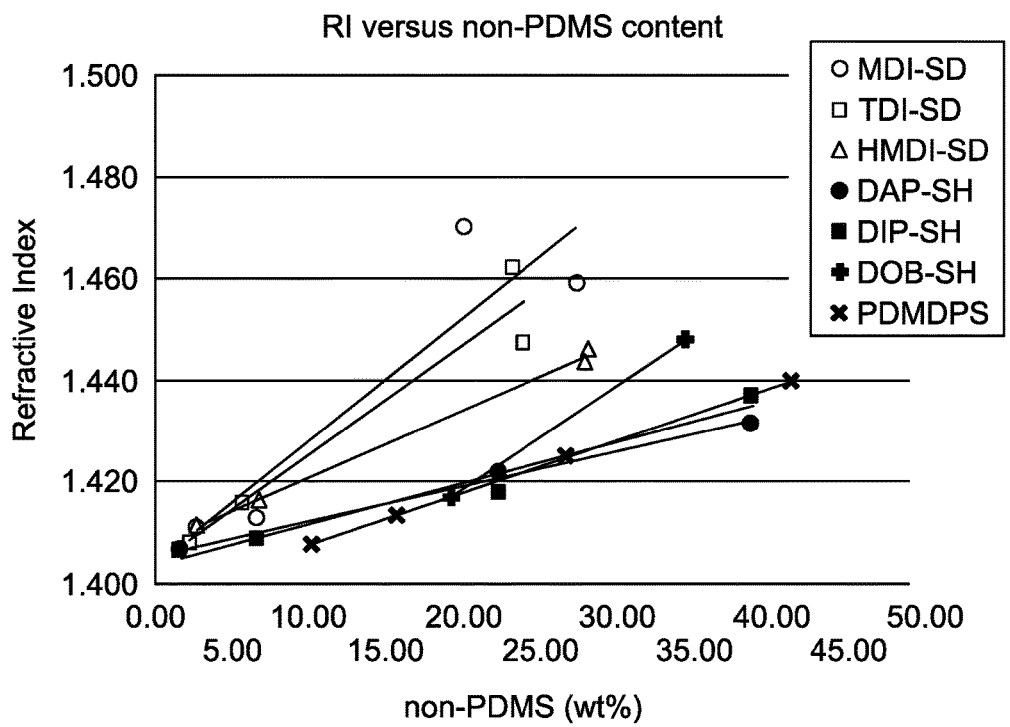
FIG. 6 depicts a graph of refractive index values versus non-PDMS content for copolymers formed in accordance with some embodiments, and poly(dimethyl-co-diphenylsiloxane) (PDMDPS).

A graph of RI values versus non-PDMS content for the copolymers prepared in this Example is shown in FIG. 6. The symbols used in FIG. 6 corresponds to the respective series of copolymers in FIG. 5. The non-PDMS content was derived from the amount of non-dimethylsiloxane units in the theoretical repeating unit of the copolymer. The non-PDMS content can be indicative of the amount of aromatic ring or aliphatic cyclic ring content in the copolymer. For example, a larger non-PDMS content correlates to a larger ring content. As can be seen in FIG. 6, the copolymers formed in this Example have generally higher RI values as compared to conventional PDMDPS material, which is consistent with the graph in FIG. 5. The TDI-SD and MDI-SD series of copolymers also exhibited the highest RI values in FIG. 6 due to the electron donating amide units adjacent to the aromatic rings in these copolymers.

In both FIGS. 5 and 6, the RI values of the copolymers prepared in this Example converged to a RI value of approximately 1.403 as they approach 0% aromatic content (FIG. 5) and 0% non-PDMS content (FIG. 6), which is the RI value for PDMDPS.

From the data in Table 3, and the graphs in FIGS. 5 and 6, it can be observed that aromatic ring or aliphatic ring structures, when incorporated in the main chain of a silicone polymer, can increase the refractive index of such materials.

The synthesized copolymers in this Example displayed higher refractive indices than that of the commercially available silicone polymer (PDMDPS). However, not all aromatic units influence the refractive index to the same extent due to the presence of electron donating linkage units adjacent to the aromatic ring. As can be noted from the copolymers in the MDI-SD and TDI-SD series, which have the electron donating amide linkage units adjacent to the ring structure, these copolymers exhibited the highest refractive indices as compared to copolymers from the other series.

Example 5

Vinyl Functional Copolymers

Incorporation of methylvinylsiloxane units into a copolymer from Example 4 may include adding DOWEX-50W-hydrogen acidic ion exchange resin (5.0 g) and a TEFLON coated magnetic stir bar to a 250 ml one-necked round-bottomed flask. The flask and its contents may be dried for 4 hours at 100° C. under vacuum. After this time, 1,3,5,7-tetravinyl-1,3,5,7-tetramethylcyclotetrasiloxane (1.0 g), and a copolymer (100 g) from Example 4 may be added to the flask. The flask may be fitted with a drying tube (DRIER-ITE) and can be heated to 70° C. The contents in the flask can be maintained at this temperature for 8 hours, after which the crude product may be diluted with THF (2:1 v,v solvent to polymer) and the DOWEX resin removed by filtration. The polymer is then precipitated with methanol, which may result in a viscous colorless polymer that includes methylvinylsiloxane repeat units within its backbone structure. The same procedure can be repeated for each of the copolymers formed in Example 4.

Example 6

Two-Part Heat Curable Systems

A method of compounding vinyl functional copolymers with silica and poly(hydromethylsiloxane-co-dimethylsiloxane) crosslinkers may include the following: treated fumed silica (AEROSIL® R812 S from Evonik Corporation, NJ, USA or CAB-O-SIL® TS-530 from Cabot Corporation, MA, USA) may be compounded into a copolymer from Example 5 using a tangential sigma blade mixer. Table 4 below shows the silica loading that may be compounded into the copolymer from Example 5. Throughout mixing, the mixer's bowl may be heated to 140° C. After an appropriate amount of silica in accordance with Table 4 has been added incrementally to the copolymer fluid, the resulting gum may be mixed for at least 2 hours. As shown in Table 4, a cross-linking catalyst and a hydromethylsiloxane copolymer (cross-linker) can be added to separate parts of the fumed silica/copolymer gum, thereby creating a two-part heat curable system made up of Parts A and B in Table 4. When Parts A and B are mixed together in equal portions, cured articles may be prepared by, for example, heating pressing at 150° C. for five minutes, and further post curing the articles in a circulating air oven at 150° C. for 2 hours. The same procedure can be repeated with any copolymer from Example 5 to form the two-part heat curable system. Examples 7 and 8 below describe exemplary cured articles prepared from the two-part heat curable system.

TABLE 4

| | Two-Part Heat Curable System | |
|---|---|---|
| | Part A | Part B |
| Silica type | CAB-O-SIL® TS-530 or AEROSIL® R812 S | CAB-O-SIL® TS-530 or AEROSIL® R812 S |
| Silica loading [parts per hundred rubber (pphr)]* | 36 | 36 |
| Copolymer from Example 5 [parts by weight] | 88 | 96 |
| Poly(hydromethylsiloxane-co-dimethylsiloxane) (Si—H cross-linker) [parts by weight] | 12 | — |
| 5% Pt complex (platinum 1,3-divinyl-1,1,3,3-tetramethyldisiloxane) in xylenes (cross linking catalyst) [parts per hundred rubber (pphr)]* | — | 4 |

*Note:
"pphr" or "parts per hundred rubber" indicates parts of a component per hundred parts of the copolymer

Example 7

Intraocular Lens

The two-part heat curable system from Example 6 may be used to form an intraocular lens. Any of the copolymers formed in Example 5, such as those derived from the TDI-SD and MDI-SD series of copolymers in Example 4, may be used to form the two-part heat curable systems in Example 6. A mold having a concave surface may be provided. A mixture containing equal portions of Parts A and B from Example 6 can be deposited as a layer on the concave surface of the mold, where it may be cured under suitable nitrogen pressures and temperatures to form a disc. The thickness of the layer should preferably be larger than the desired thickness of the completed intraocular lens. The disc can then be removed from the mold, and may be further cut and polished to a desired curvature and thickness to form the intraocular lens. The intraocular lens, when implanted into an eye of a user, is expected to correct vision of the eye and provide image clarity to the user.

Example 6

Display Screen

The two-part heat curable system from Example 6 may be used to form a flexible display screen of an electronic device. Any of the copolymers formed in Example 5, such as those derived from the TDI-SD and MDI-SD series of copolymers in Example 4, may be used to form the two-part heat curable systems in Example 6. A flat substrate may be provided where a mixture containing equal portions of Parts A and B from Example 6 can be deposited as a layer on the flat substrate. The mixture may be cured under suitable nitrogen pressures and temperatures to form a large transparent film. The film may be further cut to the desired dimensions for incorporation into the electronic device. The display screen is expected to maintain structural integrity with bending and torsional strain, and provide image clarity to a user viewing images on the device.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound comprising a copolymer of Formula I:

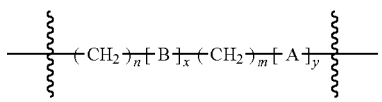

wherein:
A is selected from the group consisting of a silane and a silicate;
B is an aromatic ring containing unit or an aliphatic cyclic ring containing unit, wherein the aliphatic cyclic ring containing unit is derived from a cyclic hydroxyl carboxylic acid, a cyclic dicarboxylic acid, a cyclic diol, a cyclic diamine, a cyclic diester, a cyclic diether, or combinations thereof;
n and m are each, independently, an integer of 1 to 10; and
x and y are each, independently, an integer of 1 to 2000.

2. The compound of claim 1, wherein A comprises units derived from alkoxysilane, chlorosilane, alkoxy silicate, or combinations thereof.

3. The compound of claim 1, wherein B comprises units derived from aromatic hydroxy carboxylic acid, aromatic dicarboxylic acid, aromatic diol, aromatic aminocarboxylic acid, aromatic hydroxyamine, aromatic diamine, aromatic diisocyanate, aromatic digesters, aromatic diether, or combinations thereof.

4. The compound of claim 1, wherein B is present in the copolymer in an amount of about 5 weight percent to about 95 weight percent.

5. The compound of claim 1, wherein B comprises a linkage unit adjacent to the aromatic ring or the aliphatic cyclic ring, and wherein the linkage unit is an amide linkage unit, an ester linkage unit, an ether linkage unit, or combinations thereof.

6. The compound of claim 1, further comprising units derived from copolymerizable monomers selected from the group consisting of cyclic dicarboxylic acids, aliphatic diols, cyclic diols, aromatic mercapto carboxylic acids, aromatic dithiols, aromatic mercapto phenols, or combinations thereof.

7. The compound of claim 1, wherein the copolymer is crosslinked.

8. The compound of claim 1, further comprising one or more crosslinking agents or one or more curing agents comprising an epoxy functional crosslinker, a phenolic functional crosslinker, a hydroxyl functional crosslinker, an amine functional crosslinker, a carboxylate functional crosslinker, an isocyanate functional crosslinker, or combinations thereof, covalently associated with the copolymer.

9. The compound of claim 1, wherein Formula I further comprises Formula III:

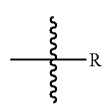

wherein R is an end group defining a terminus of the copolymer and wherein R comprises vinyl, alkoxy, acetoxy, methoxy, amide, ester, carbamate, enoxy, oxime, amino, hydroxyl, cyano, halo, acrylate, epoxide, isocyanato, hydride, or combinations thereof.

10. The compound of claim 1, wherein the copolymer exhibits a refractive index of about 1 to about 2.42.

11. An article of manufacture comprising a copolymer of Formula I:

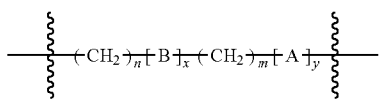

wherein:
A is selected from the group consisting of a silane and a silicate;
B is an aromatic ring containing unit or an aliphatic cyclic ring containing unit, wherein the aliphatic cyclic ring containing unit is derived from a cyclic hydroxyl carboxylic acid, a cyclic dicarboxylic acid, a cyclic diol, a cyclic diamine, a cyclic diester, a cyclic diether, or combinations thereof;
n and m are each, independently, an integer of 1 to 10; and
x and y are each, independently, an integer of 1 to 2000.

12. The article of manufacture of claim 11, wherein Formula I further comprises Formula III:

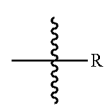

wherein R is an end group defining a terminus of the copolymer and wherein R comprises vinyl, alkoxy, acetoxy, methoxy, amide, ester, carbamate, enoxy, oxime, amino, hydroxyl, cyano, halo, acrylate, epoxide, isocyanato, or combinations thereof.

13. The article of manufacture of claim 11, wherein the article of manufacture comprises a display.

14. The article of manufacture of claim 11, wherein the article of manufacture comprises an electronic device.

15. The article of manufacture of claim 14, wherein the electronic device comprises a personal computer, a gaming system, a television, a portable electronic device, a smartphone, a personal digital assistant, a camera, a tablet computer, a laptop computer, a GPS navigation device, a media player, or a combination thereof.

16. The article of manufacture of claim 11, wherein the article of manufacture comprises a contact lens, an intraocular lens, an overlay lens, an ocular insert, an optical insert, or a combination thereof.

17. The article of manufacture of claim 11, wherein the copolymer exhibits a refractive index of about 1 to about 2.42.

18. An ophthalmic lens comprising a copolymer of Formula I:

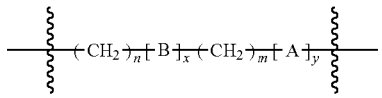 (I)

wherein:
- A is selected from the group consisting of a silane and a silicate;
- B is an aromatic ring containing unit or an aliphatic cyclic ring containing unit, wherein the aliphatic cyclic ring containing unit is derived from a cyclic hydroxyl carboxylic acid, a cyclic dicarboxylic acid, a cyclic diol, a cyclic diamine, a cyclic diester, a cyclic diether, or combinations thereof;
- n and m are each, independently, an integer of 1 to 10; and
- x and y are each, independently, an integer of 1 to 2000.

19. The ophthalmic lens of claim 18, wherein the lens is a contact lens, an intraocular lens, an overlay lens, an ocular insert, or an optical insert.

20. The ophthalmic lens of claim 18, wherein Formula I further comprises Formula III:

 (III)

wherein R is an end group defining a terminus of the copolymer and wherein R comprises vinyl, alkoxy, acetoxy, methoxy, amide, ester, carbamate, enoxy, oxime, amino, hydroxyl, cyano, halo, acrylate, epoxide, isocyanato, or combinations thereof.

21. The ophthalmic lens of claim 18, wherein the copolymer exhibits a refractive index of about 1 to about 2.42.

* * * * *

UNITED STATES PATENT AND TRADEMARK OFFICE
CERTIFICATE OF CORRECTION

PATENT NO. : 9,840,595 B2
APPLICATION NO. : 14/411025
DATED : December 12, 2017
INVENTOR(S) : Tapsak It is certified that error appears in the above-identified patent and that said Letters Patent is hereby corrected as shown below:

In the Specification

In Column 3, Lines 16-19, delete "FIG. 5 depicts a graph of refractive index values vesus aromatic content for copolymers formed in accordance with some embodiments, and poly(dimethyl-co-diphenylsiloxane) (PDMDPS)." and insert
-- FIG. 5 depicts a chart of various copolymers prepared, according to some embodiments. --, therefor.

In Column 3, Lines 20-23, delete "FIG. 6 depicts a graph of refractive index values vesus non-PDMS content for copolymers formed in accordance with some embodiments, and poly(dimethyl-co-diphenylsiloxane) (PDMDPS).".

In Column 17, Line 42, delete "and HTS." and insert -- and HT5. --, therefor.

In Column 22, Line 16, delete "HMDI and" and insert -- HMDI, and --, therefor.

In Columns 27-28, Lines 57-2, delete "A graph of refractive index (RI) values plotted versus the aromatic ring content, or aliphatic ring content in the case of HMDI, for all series of copolymers prepared in this Example is shown in FIG.5. In FIG. 5, the unfilled round symbol "○" represents the MDI-SD series of copolymers, the unfilled square symbol "□" represents the TDI-SD series of copolymers, the unfilled triangle symbol "Δ" represents the HMDI-SD series of copolymers, the filled square symbol "●" represents the DAP-SH series of copolymers, the filled square symbol "■" represents the DIP-SH series of copolymers, the plus symbol "+" represents the DOB-SH series of copolymers, and the cross symbol "x" represents the PDMDPS copolymer. It can be noted from FIG. 5 that the" and insert -- It can be noted from Table 3 that the --, therefor.

In Column 28, Line 10, delete "noted from FIG. 5 that" and insert -- noted that --, therefor.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,840,595 B2

In Column 28, Lines 43-45, delete "A graph of RI values versus non-PDMS content for the copolymers prepared in this Example is shown in FIG. 6. The symbols used in FIG. 6 corresponds to the respective series of copolymers in FIG. 5. The non-PDMS" and insert -- The non-PDMS --, therefor.

In Column 28, Line 52, delete "As can be seen in FIG. 6, the" and insert -- The --, therefor.

In Column 28, Lines 54-55, delete "material, which is consistent with the graph in FIG. 5." and insert -- material. --, therefor.

In Column 28, Line 57, delete "values in FIG. 6 due" and insert -- values due --, therefor.

In Column 28, Line 59, delete "In both FIGS. 5 and 6, the" and insert -- The --, therefor.

In Column 28, Lines 62-63, delete "(FIG. 5) and 0% non-PDMS content (FIG.6), which is the RI value for PDMDPS." and insert -- (Table 3). --, therefor.

In Column 28, Lines 64-65, delete "Table 3, and the graphs in FIGS. 5 and 6, it" and insert -- Table 3, it --, therefor.

In the Claims

In Column 31, Line 33, in Claim 3, delete "digesters," and insert -- diesters, --, therefor.